(12) United States Patent
Aebi et al.

(10) Patent No.: US 9,636,338 B2
(45) Date of Patent: May 2, 2017

(54) PHENYL-DIHYDROPYRIDINE DERIVATIVES AS INHIBITORS OF ALDOSTERONE SYNTHASE

(71) Applicant: Hoffmann-La Roche Inc., Little Falls, NJ (US)

(72) Inventors: Johannes Aebi, Binningen (CH); Kurt Amrein, Itingen (CH); Robert Britton, North Vancouver (CA); Benoit Hornsperger, Altkirch (FR); Bernd Kuhn, Reinach BL (CH); Hans P. Maerki, Basel (CH); Rainer E. Martin, Basel (CH); Alexander V. Mayweg, Basel (CH); Xuefei Tan, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/098,737

(22) Filed: Apr. 14, 2016

(65) Prior Publication Data

US 2016/0221954 A1     Aug. 4, 2016

Related U.S. Application Data

(63) Continuation of application No. PCT/EP2014/071940, filed on Oct. 14, 2014.

(30) Foreign Application Priority Data

Oct. 17, 2013   (WO) ................ PCT/CN2013/085412

(51) Int. Cl.
| | | |
|---|---|---|
| *A61K 31/472* | (2006.01) | |
| *C07D 217/02* | (2006.01) | |
| *C07D 221/04* | (2006.01) | |
| *C07D 401/12* | (2006.01) | |
| *C07D 413/12* | (2006.01) | |

(52) U.S. Cl.
CPC .......... *A61K 31/472* (2013.01); *C07D 217/02* (2013.01); *C07D 221/04* (2013.01); *C07D 401/12* (2013.01); *C07D 413/12* (2013.01)

(58) Field of Classification Search
CPC ............................ A61K 31/472; C07D 217/02

USPC .......................................... 514/307; 546/139
See application file for complete search history.

(56) References Cited

U.S. PATENT DOCUMENTS 9,197,429 B1 * 11/2015 Heninwolf .......... H04L 12/1872

FOREIGN PATENT DOCUMENTS

| WO | 2005/118581 A1 | 12/2005 |
| WO | 2013/041591 A1 | 3/2013 |

OTHER PUBLICATIONS

HCAPLUS abstract of Neunhoeffer et al, Heterocycles (1993), vol. 35 (2), pp. 1089-10101.*
ISR for PCT/EP2014/071940.
Neunhoeffer et al., "Cycloaddition Reactions with Azabenzenes, XVIII, Synthesis of [2] Pyrindines" Heterocycles 35(2):1089-1101 (1993).
Written Opinion for PCT/EP2014/071940.

* cited by examiner

*Primary Examiner* — Kamal Saeed
*Assistant Examiner* — Janet L Coppins

(57) ABSTRACT

The invention provides novel compounds having the general formula (I)

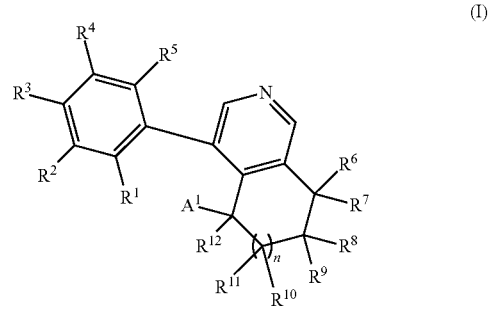

wherein $R^1$, $R^2$, $R^3$, $R^4$, $R^5$, $R^6$, $R^7$, $R^8$, $R^9$, $R^{10}$, $R^{11}$, $R^{12}$, $A^1$ and n are as described herein, compositions including the compounds and methods of using the compounds.

19 Claims, No Drawings

PHENYL-DIHYDROPYRIDINE DERIVATIVES AS INHIBITORS OF ALDOSTERONE SYNTHASE

RELATED APPLICATION DATA

This application is a Continuation of International Application No. PCT/EP2014/071940 filed on Oct. 14, 2014, which claims priority to International Application No. PCT/CN2013/085412 filed on Oct. 17, 2013, the disclosures of which are incorporated herein by reference in their entirety.

The present invention relates to organic compounds useful for therapy or prophylaxis in a mammal, and in particular to aldosterone synthase inhibitors for the treatment or prophylaxis of chronic kidney disease, congestive heart failure, hypertension, primary aldosteronism and Cushing syndrome.

The present invention provides novel compounds of formula (I)

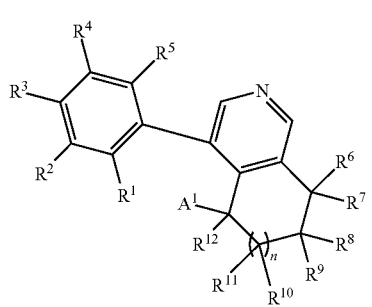

wherein
$R^1$, $R^2$, $R^3$, $R^4$ and $R^5$ are independently selected from H, halogen, cyano, nitro, alkyl, haloalkyl, cycloalkyl, alkoxy, haloalkoxy and cycloalkoxy;
$R^6$, $R^7$, $R^8$, $R^9$, $R^{10}$ and $R^{11}$ are independently selected from H, halogen, alkyl and haloalkyl;
$R^{12}$ is H, alkyl, haloalkyl, cycloalkyl, substituted aryl or substituted heteroaryl, wherein substituted aryl or substituted heteroaryl are substituted with $R^{18}$, $R^{19}$ and $R^{20}$;
$A^1$ is —$(CR^{14}R^{15})_p$—$NR^{16}R^{17}$, —$(CR^{14}R^{15})_p$—$OR^{17}$, —$(CR^{14}R^{15})_p$—$C(O)NR^{16}R^{17}$ or —$(CR^{14}R^{15})_p$—$C(O)OR^{17}$;
$R^{14}$ and $R^{15}$ are independently selected from H, alkyl, haloalkyl, cycloalkyl and halocycloalkyl;
$R^{16}$ is H, alkyl, haloalkyl, cycloalkyl, hydroxyalkyl, alkoxyalkyl or haloalkoxyalkyl;
$R^{17}$ is H, alkyl, haloalkyl, cycloalkyl, cycloalkylalkyl, alkoxyalkyl, cycloalkoxyalkyl, substituted aryl or substituted heteroaryl, wherein substituted aryl and substituted heteroaryl are substituted with $R^{21}$, $R^{22}$ and $R^{23}$;
or $R^{16}$ and $R^{17}$ together with the nitrogen to which they are attached form a substituted heterocycloalkyl or a substituted heteroaryl, wherein substituted heterocycloalkyl and substituted heteroaryl are substituted with $R^{21}$, $R^{22}$ and $R^{23}$;
$R^{18}$, $R^{19}$, $R^{20}$, $R^{21}$, $R^{22}$ and $R^{23}$ are independently selected from H, halogen, alkyl, haloalkyl, cycloalkyl, alkoxy and haloalkoxy;
n is zero, 1 or 2;
p is zero, 1 or 2;
and pharmaceutically acceptable salts thereof.

Herein we describe inhibitors of aldosterone synthase that have the potential to protect from organ/tissue damage caused by an absolute or relative excess of aldosterone. Hypertension affects about 20% of the adult population in developed countries. In persons 60 years and older, this percentage increases to above 60%. Hypertensive subjects display an increased risk of other physiological complications including stroke, myocardial infarction, atrial fibrillation, heart failure, peripheral vascular disease and renal impairment. The renin angiotensin aldosterone system is a pathway that has been linked to hypertension, volume and salt balance and more recently to contribute directly to end organ damage in advanced stages of heart failure or kidney disease. ACE inhibitors and angiotensin receptor blockers (ARBs) are successfully used to improve duration and quality of life of patients. These drugs are not yielding maximum protection. In a relatively large number of patients ACE and ARB's lead to so-called aldosterone breakthrough, a phenomenon where aldosterone levels, after a first initial decline, return to pathological levels. It has been demonstrated that the deleterious consequences of inappropriately increased aldosterone levels (in relation to salt intake/levels) can be minimized by aldosterone blockade with mineralocorticoid receptor antagonists. A direct inhibition of aldosterone synthesis is expected to provide even better protection as it will also reduce non-genomic effects of aldosterone as well.

The effects of aldosterone on Na/K transport lead to increased re-absorption of sodium and water and the secretion of potassium in the kidneys. Overall this results in increased blood volume and, therefore, increased blood pressure. Beyond its role in the regulation of renal sodium re-absorption aldosterone can exert deleterious effects on the kidney, the heart and the vascular system especially in a "high sodium" context. It has been shown that under such conditions aldosterone leads to increased oxidative stress which ultimately may contribute to organ damage. Infusion of aldosterone into renally compromised rats (either by high salt treatment or by unilaterally nephrectomy) induces a wide array of injuries to the kidney including glomerular expansion, podocyte injury, interstitial inflammation, mesangial cell proliferation and fibrosis reflected by proteinuria. More specifically aldosterone was shown to increase the expression of the adhesion molecule ICAM-1 in the kidney. ICAM-1 is critically involved in glomerular inflammation. Similarly, aldosterone was shown to increase the expression of inflammatory cytokines, such as interleukin IL-1b and IL-6, MCP-1 and osteopontin. On a cellular level it was demonstrated that in vascular fibroblasts aldosterone increased the expression of type I collagen mRNA, a mediator of fibrosis. Aldosterone also stimulates type IV collagen accumulation in rat mesangial cells and induces plasminogen activator inhibitor-1 (PAI-1) expression in smooth muscle cells. In summary aldosterone has emerged as a key hormone involved in renal damage. Aldosterone plays an equally important role in mediating cardiovascular risk.

There is ample preclinical evidence that MR-antagonists (spironolactone and eplerenone) improve blood pressure, cardiac and renal function in various pre-clinical models.

More recently preclinical studies highlight the important contribution of CYP11B2 to cardiovascular and renal morbidity and mortality. The CYP11B2 inhibitor FAD286 and the MR antagonist spironolactone were evaluated in a rat model of chronic kidney disease (high angiotensin II exposure; high salt and uni-nephrectomy). Angiotensin II and high salt treatment caused albuminuria, azotemia, renovascular hypertrophy, glomerular injury, increased PAI-1, and osteopontin mRNA expression, as well as tubulointerstitial fibrosis. Both drugs prevented these renal effects and attenuated cardiac and aortic medial hypertrophy. Following 4 weeks of treatment with FAD286, plasma aldosterone was reduced, whereas spironolactone increased aldosterone at 4 and 8 weeks of treatment. Similarly only spironolactone but not FAD286 enhanced angiotensin II and salt-stimulated PAI-1 mRNA expression in the aorta and the heart. In other studies the CYP11B2 inhibitor FAD286 improved blood pressure and cardiovascular function and structure in rats with experimental heart failure. In the same studies FAD286 was shown to improve kidney function and morphology.

Administration of an orally active CYP11B2 inhibitor, LCI699, to patients with primary aldosteronism, lead to the conclusion that it effectively inhibits CYP11B2 in patients with primary aldosteronism resulting in significantly lower circulating aldosterone levels and that it corrected the hypokalemia and mildly decreased blood pressure. The effects on the glucocorticoid axis were consistent with a poor selectivity of the compound and a latent inhibition of cortisol synthesis. Taken together these data support the concept that a CYP11B2 inhibitor can lower inappropriately high aldosterone levels. Achieving good selectivity against CYP11B1 is important to be free of undesired side effects on the HPA axis and will differentiate different CYP11B2 inhibitors.

The compounds of the present invention according formula (I) are potent inhibitors of CYPB11B2 and present an improved selectivity towards CYP11B2 versus CYP11B1 combined with an improved metabolic stability.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of chronic kidney disease, congestive heart failure, hypertension, primary aldosteronism and Cushing syndrome and the use of the said compounds, salts or esters for the production of medicaments for the treatment or prophylaxis of chronic kidney disease, congestive heart failure, hypertension, primary aldosteronism and Cushing syndrome.

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular alkoxy group include methoxy.

The term "alkoxyalkyl" denotes an alkyl group wherein at least one of the hydrogen atoms of the alkyl group has been replaced by an alkoxy group. Exemplary alkoxyalkyl groups include methoxymethyl, ethoxymethyl, methoxyethyl, ethoxyethyl, methoxypropyl, ethoxypropyl and isopropoxymethyl. Particular alkoxyalkyl group is methoxyethyl.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl and isopropyl, n-butyl, iso-butyl, sec-butyl, and. Particular alkyl groups include methyl, ethyl and propyl.

The term "aryl" denotes a monovalent aromatic carbocyclic mono- or bicyclic ring system comprising 6 to 10 carbon ring atoms. Examples of aryl moieties include phenyl and naphthyl. Particular aryl group is phenyl.

The term "cyano" denotes a —C≡N group.

The term "cycloalkoxy" denotes a group of the formula —O—R', wherein R' is a cycloalkyl group. Examples of cycloalkoxy group include cyclopropoxy, cyclobutoxy, cyclopentyloxy, cyclohexyloxy, cycloheptyloxy and cyclooctyloxy. Particular cycloalkoxy group is cyclopropoxy.

The term "cycloalkoxyalkyl" denotes an alkyl group wherein at least one of the hydrogen atoms of the alkyl group has been replaced by a cycloalkoxy group. Examples of cycloalkoxyalkyl groups include cyclopropoxymethyl, cyclopropoxyethyl, cyclobutoxymethyl, cyclobutoxyethyl, cyclopentyloxymethyl, cyclopentyloxyethyl, cyclohexyloxymethyl, cyclohexyloxyethyl, cycloheptyloxymethyl, cycloheptyloxyethyl, cyclooctyloxymethyl and cyclooctyloxyethyl.

The term "cycloalkyl" denotes a monovalent saturated monocyclic hydrocarbon group of 3 to 10 ring carbon atoms. In particular embodiments, cycloalkyl denotes a monovalent saturated monocyclic hydrocarbon group of 3 to 8 ring carbon atoms. Examples for cycloalkyl are cyclopropyl, cyclobutanyl, cyclopentyl, cyclohexyl or cycloheptyl. Particular cycloalkyl group is cyclopropyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclopropylbutyl, cyclobutylpropyl, 2-cyclopropylbutyl, cyclopentylbutyl, cyclohexylmethyl, cyclohexylethyl, bicyclo[4.1.0]heptanylmethyl, bicyclo[4.1.0]heptanylethyl, bicyclo[2.2.2]octanylmethyl, bicyclo[2.2.2]octanylethyl, adamantanylmethyl and adamantanylethyl.

The term "haloalkoxy" denotes an alkoxy group wherein at least one of the hydrogen atoms of the alkoxy group has been replaced by same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy.

The term "haloalkoxyalkyl" denotes an alkyl group wherein at least one of the hydrogen atoms of the alkyl group has been replaced by a haloalkoxy group. Examples of haloalkoxyalkyl include fluoromethoxymethyl, difluoromethoxymethyl, trifluoromethoxymethyl, fluoroethoxymethyl, difluoroethoxymethyl, trifluoroethoxymethyl, fluoromethoxyethyl, difluoromethoxyethyl, trifluoromethoxyethyl, fluoroethoxyethyl, difluoroethoxyethyl, trifluoroethoxyethyl, fluoromethoxypropyl, difluoromethoxypropyl, trifluoromethoxypropyl, fluoroethoxypropyl, difluoroethoxypropyl and trifluoroethoxypropyl.

The term "haloalkyl" denotes an alkyl group wherein at least one of the hydrogen atoms of the alkyl group has been replaced by same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl group is trifluoromethyl.

The term "halocycloalkyl" denotes a cycloalkyl group wherein at least one of the hydrogen atoms of the cycloalkyl group has been replaced by same or different halogen atoms, particularly fluoro atoms. Examples of halocycloalkyl groups include fluorocyclopropyl, difluorocyclopropyl, fluorocyclobutyl and difluorocyclobutyl.

The term "halogen" and "halo" are used interchangeably herein and denote fluoro, chloro, bromo, or iodo. Particular halogens are chloro and fluoro. Particular halogen is fluoro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl and quinoxalinyl. Particular heteroaryl groups are isoxazolyl and pyrazolyl.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocycloalkyl are 4,5-dihydro-oxazolyl, oxetanyl, azetidinyl, pyrrolidinyl, 2-oxo-pyrrolidin-3-yl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydrooxazolyl, tetrahydro-pyridinyl, or dihydropyranyl. Further particular example of heterocycloalkyl groups are pyrrolidinyl, piperidinyl and morpholinyl.

The term "hydroxy" denotes an —OH group.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxypropyl, hydroxymethylpropyl and dihydroxypropyl.

The term "nitro" denotes a —NO$_2$ group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. μ Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxycarbonyl (Fmoc). More particular protecting group is the tert-butoxycarbonyl (Boc).

The abbreviation uM means microMolar and is equivalent to the symbol μM.

The compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^2$H ("D"), $^3$H ("T"), $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically labeled compounds of the present invention (e.g., those labeled with $^3$H or $^{14}$C) are useful in compound and/or substrate tissue distribution assays. Tritiated ($^3$H) and carbon-14 ($^{14}$C) isotopes are useful for their ease of preparation and detectability. Further substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of the present inventions can generally be prepared by following procedures analogous to those disclosed in the Schemes and/or in the Examples herein below, by substituting a non-isotopically labeled reagent with a isotopically labeled reagent. In particular, compounds of formula (I) wherein one or more H atom have been replaced by a $^2$H atom are also an embodiment of this invention.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

Also an embodiment of the present invention are compounds according to formula (I) as described herein wherein $R^1$, $R^2$, $R^3$, $R^4$ and $R^5$ are independently selected from H, halogen and haloalkyl.

A particular embodiment of the present invention are compounds according to formula (I) as described herein, wherein $R^1$ and $R^2$ are independently selected from H and halogen.

A further particular embodiment of the present invention are compounds according to formula (I) as described herein, wherein $R^3$ is haloalkyl.

In a further embodiment of the present invention are compounds according to formula (I) as described herein, wherein $R^4$ and $R^5$ are H.

Another further embodiment of the present invention are compounds according to formula (I) as described herein, wherein n is zero and $R^6$, $R^7$, $R^8$ and $R^9$ are H.

Another embodiment of the present invention are compounds according to formula (I) as described herein, wherein $R^{12}$ is H, alkyl or substituted aryl, wherein substituted aryl is substituted with $R^{18}$, $R^{19}$ and $R^{20}$.

Another particular embodiment of the present invention are compounds according to formula (I) as described herein, wherein $R^{18}$, $R^{19}$ and $R^{20}$ are H.

A more particular embodiment of the present invention are compounds according to formula (I) as described herein, wherein $A^1$ is —$(CR^{14}R^{15})_p$—$OR^{17}$ or —$(CR^{14}R^{15})_p$—C(O)$NR^{16}R^{17}$.

A particular embodiment of the present invention are compounds according to formula (I) as described herein, wherein $A^1$ is —$(CR^{14}R^{15})_p$—$OR^{17}$.

Another particular embodiment of the present invention are compounds according to formula (I) as described herein, wherein $R^{16}$ is H.

Also a particular embodiment of the present invention are compounds according to formula (I) as described herein, wherein $R^{17}$ is H, alkyl, alkoxyalkyl or substituted heteroaryl, wherein substituted heteroaryl is substituted with $R^{21}$, $R^{22}$ and $R^{23}$ or $R^{16}$ and $R^{17}$ together with the nitrogen to which they are attached form a substituted heterocycloalkyl, wherein substituted heterocycloalkyl is substituted with $R^{21}$, $R^{22}$ and $R^{23}$.

Another embodiment of the present invention are compounds according to formula (I) as described herein, wherein $R^{17}$ is H, alkyl, alkoxyalkyl or substituted heteroaryl, wherein substituted heteroaryl is substituted with $R^{21}$, $R^{22}$ and $R^{23}$.

Another particular embodiment of the present invention are compounds according to formula (I) as described herein, wherein $R^{21}$, $R^{22}$ and $R^{23}$ are independently selected from H and alkyl.

A further particular embodiment of the present invention are compounds according to formula (I) as described herein, wherein $R^{14}$ and $R^{15}$ are H.

A more particular embodiment of the present invention are compounds according to formula (I) as described herein, wherein p is zero or 1.

Particular examples of compounds of formula (I) as described herein are selected from 4-(3-fluoro-4-(trifluoromethyl)phenyl)-6,7-dihydro-5H-cyclopenta[c]pyridin-5-amine;

4-(3-fluoro-4-(trifluoromethyl)phenyl)-6,7-dihydro-5H-cyclopenta[c]pyridin-5-ol;

4-(3-fluoro-4-(trifluoromethyl)phenyl)-5-methyl-6,7-dihydro-5H-cyclopenta[c]pyridin-5-ol;

4-(3-fluoro-4-(trifluoromethyl)phenyl)-5-phenyl-6,7-dihydro-5H-cyclopenta[c]pyridin-5-ol;

4-(2-fluoro-4-(trifluoromethyl)phenyl)-6,7-dihydro-5H-cyclopenta[c]pyridin-5-ol;

4-(2-fluoro-4-(trifluoromethyl)phenyl)-5-methyl-6,7-dihydro-5H-cyclopenta[c]pyridin-5-ol;

4-(2-fluoro-4-(trifluoromethyl)phenyl)-5-isopropyl-6,7-dihydro-5H-cyclopenta[c]pyridin-5-ol;

4-(2-fluoro-4-(trifluoromethyl)phenyl)-5-phenyl-6,7-dihydro-5H-cyclopenta[c]pyridin-5-ol;

(+)-4-(2-fluoro-4-(trifluoromethyl)phenyl)-5-phenyl-6,7-dihydro-5H-cyclopenta[c]pyridin-5-ol;

(−)-4-(2-fluoro-4-(trifluoromethyl)phenyl)-5-phenyl-6,7-dihydro-5H-cyclopenta[c]pyridin-5-ol;

(R)-4-(2-fluoro-4-(trifluoromethyl)phenyl)-5-phenyl-6,7-dihydro-5H-cyclopenta[c]pyridin-5-ol;

(S)-4-(2-fluoro-4-(trifluoromethyl)phenyl)-5-phenyl-6,7-dihydro-5H-cyclopenta[c]pyridin-5-ol;

ethyl 2-(4-(3-fluoro-4-(trifluoromethyl)phenyl)-6,7-dihydro-5H-cyclopenta[c]pyridin-5-yl)acetate;

2-(4-(3-fluoro-4-(trifluoromethyl)phenyl)-6,7-dihydro-5H-cyclopenta[c]pyridin-5-yl)-N-methylacetamide;

N-(cyclopropylmethyl)-2-(4-(3-fluoro-4-(trifluoromethyl)phenyl)-6,7-dihydro-5H-cyclopenta[c]pyridin-5-yl)acetamide;

2-(4-(3-fluoro-4-(trifluoromethyl)phenyl)-6,7-dihydro-5H-cyclopenta[c]pyridin-5-yl)-N-propylacetamide;

2-(4-(3-fluoro-4-(trifluoromethyl)phenyl)-6,7-dihydro-5H-cyclopenta[c]pyridin-5-yl)-1-(piperidin-1-yl)ethanone;

2-(4-(3-fluoro-4-(trifluoromethyl)phenyl)-6,7-dihydro-5H-cyclopenta[c]pyridin-5-yl)-1-morpholinoethanone;

2-[4-(3-Fluoro-4-trifluoromethyl-phenyl)-6,7-dihydro-5H-[2]pyrindin-5-yl]-N-isoxazol-3-yl-acetamide;

2-(4-(3-fluoro-4-(trifluoromethyl)phenyl)-6,7-dihydro-5H-cyclopenta[c]pyridin-5-yl)-N-(1H-pyrazol-3-yl)acetamide;

2-(4-(2-fluoro-4-(trifluoromethyl)phenyl)-6,7-dihydro-5H-cyclopenta[c]pyridin-5-yl)-1-(pyrrolidin-1-yl)ethanone;

N-ethyl-2-(4-(2-fluoro-4-(trifluoromethyl)phenyl)-6,7-dihydro-5H-cyclopenta[c]pyridin-5-yl)-N-methylacetamide;

2-(4-(2-fluoro-4-(trifluoromethyl)phenyl)-6,7-dihydro-5H-cyclopenta[c]pyridin-5-yl)-N-isopropyl-N-methylacetamide;

N-cyclopropyl-2-(4-(2-fluoro-4-(trifluoromethyl)phenyl)-6,7-dihydro-5H-cyclopenta[c]pyridin-5-yl)-N-methylacetamide;

N-cyclopropyl-N-ethyl-2-(4-(2-fluoro-4-(trifluoromethyl)phenyl)-6,7-dihydro-5H-cyclopenta[c]pyridin-5-yl)acetamide;

2-(4-(2-fluoro-4-(trifluoromethyl)phenyl)-6,7-dihydro-5H-cyclopenta[c]pyridin-5-yl)1-((S)-2-methylpyrrolidin-1-yl)ethanone;

and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the persons skilled in the art such as e.g. chiral chromatography or crystallization. The substituents and indices used in the following description of the processes have the significance given herein.

The following abbreviations are used in the present text:
BH$_3$=borane, CDI=1,1-carbonyldiimidazole, DBU=2,3,4,6,7,8,9,10-octahydro-pyrimido[1,2-α]azepine, DCC=N,N'-dicyclohexylcarbodiimide, DCM=dichloromethane, DMAP=4-dimethylaminopyridine, DMF=N,N-dimethylformamide, EDCI=1-(3-dimethyl-aminopropyl)-3-ethylcarbodiimide hydrochloride, EtOAc=ethyl acetate, h=hour, HATU=1-[bis(dimethylamino)methylene]-1H-1,2,3-triazolo[4,5-b]pyridinium-3-oxide hexafluorophosphate, HPLC=high performance liquid chromatography, HOBT=1-hydroxy-1,2,3-benzotriazole, Huenig's base=iPr$_2$NEt=N-ethyl diisopropylamine, LiAlH$_4$=lithium aluminium hydride, LiBH$_4$=lithium borohydride, MeOH=methanol, MPLC=medium pressure liquid chromatography, NaBH$_3$CN=sodium cyanoborohydride, NaBH$_4$=sodium borohydride, NaBH(OAc)$_3$=sodium triacetoxyborohydride, NH$_4$OAc=ammonium acetate, rt=room temperature, TBTU=O-benzotriazol-1-yl-N,N,N',N'-tetramethyl-uronium tetrafluoroborate, TosMIC=toluenesulfonylmethyl isocyanide, THF=tetrahydrofuran.

Compounds of formula (I) can be prepared by cycloaddition reaction of oxazoles 1 with cyclopentenes 2 at elevated temperatures (Scheme 1, step a). This particular inverse-electron-demand hetero-/retro-Diels-Alder reaction (for a recent review on ihDA/rDA reactions see: R. A. A. Foster, M. C. Willis, Chem. Soc. Rev. 2013, 42, 63) also known as the Kondrat'eva reaction (see: J. I. Levin, S. M. Weinreb, J. Org. Chem. 1984, 49, 4325) provides convenient access to annulated pyridines (J. Lehmann, T. Alzieu, R. E. Martin, R. Britton, Org. Lett. 2013, 15, 3550). Similarly, the reaction can be conducted with the corresponding cyclohexenes or cycloheptenes replacing cyclopentenes 2. 5-Aryl substituted oxazoles (1) are either commercially available or can be prepared by methods known to persons skilled in the art such as from aryl aldehydes and TosMIC (F. Besselièvre, F. Mahuteau-Betzer, D. S. Grierson, S. Piguel, J. Org. Chem. 2008, 73, 3278) in the presence of a base such as potassium carbonate and a solvent like methanol or by direct regioselective palladium(0)-catalyzed arylation of oxazole in the presence of a base such as potassium carbonate, pivalic acid and a phosphine ligand like 3,4,5,6-tetramethyl-tert-Bu-X-Phos in a polar solvent such as dimethyl acetamide or dimethyl formamide (N. A. Strotman, H. R. Chobanian, Y. Guo, J. He, J. E. Wilson, Org. Lett. 2010, 12, 3278). The Kondrat'eva reaction can be conducted under classical batch conditions (i.e. heating by microwave irradiation) or more preferably under continuous flow conditions. The use of continuous flow conditions is particularly preferable due to the high volatility (i.e. low boiling point) of alkenes of general structure 2 used in this transformation. Preferably the reaction is conducted in an apolar solvent such as toluene, chlorobenzene or trifluoromethyl benzene and in a temperature range between 150° C. and 280° C., more preferably between 200° C. and 280° C., and in the presence of an acid such as trifluoroacetic acid. In case of R$^6$, R$^7$, R$^{12}$ and B are different from H, the desired isomer 3 might be separated from regioisomeric mixtures by means of chromatography such as silica column chromatography, MPLC or preparative HPLC.

Annulated pyridines 3 (R$^{12}$ and B are H) can be oxidized under mild conditions selectively in the benzylic position to give desired ketones 4 with hydroperoxides such as tert-butyl hydroperoxide (TBHP) in the presence of a mixed-valent dirhodium(II, III) tetrakis caprolactamate catalyst (preparation of catalyst described in: M. P. Doyle, L. J. Westrum, W. N. E. Wolthuis, M. M. See, W. P. Boone, V. Bagheri, M. M. Pearson, J. Am. Chem. Soc. 1993, 115, 958) and a base such as sodium bicarbonate (A. J. Catino, J. M. Nichols, H. Choi, S. Gottipamula, M. P. Doyle, Org. Lett. 2005, 7, 5167; Scheme 1, step b). The required regioisomer 4a can be separated from the undesirable isomer 4b by classical purification methods such as silica column chromatography, medium pressure liquid chromatography (MPLC) or high-pressure liquid chromatography (HPLC). Alternatively, oxidation in the benzylic position of compounds of structure 3 affording the corresponding alcohols 5 can be achieved by an in situ hydroperoxide quench procedure using lithium bis(trimethylsilyl)amide (LiHMDS) as a base and in the presence of triethyl phosphite and dry oxygen (N. Catozzi, M. G. Edwards, S. A. Raw, P. Wasnaire, R. J. K. Taylor, J. Org. Chem. 2009, 74, 8343; Scheme 1, step c). Enantiomers or diastereoisomers produced during this reaction can be separated by methods known to the man skilled in the art such as e.g. chiral chromatography or crystallization.

Scheme 1

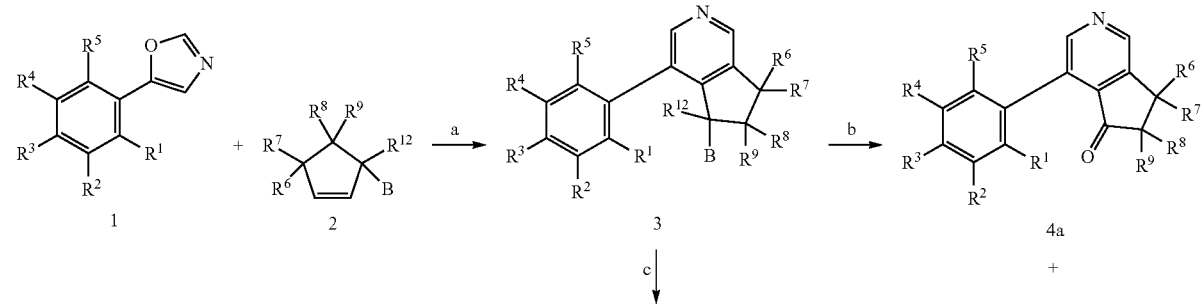

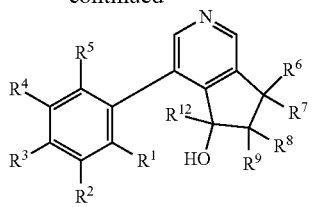
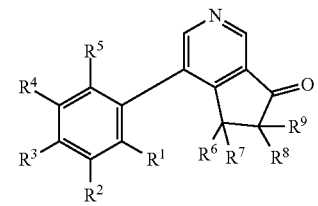

Ketones 4a can be converted to amines of type 6 ($R^{12}$ is H) by suitable reductive amination procedures (e.g., Leuckart-Wallach reaction) such as by treatment with appropriate amines, e.g. NH$_4$OAc or ammonia in methanol or ethanol and a reducing agent such as NaBH$_4$, LiBH$_4$, NaBH$_3$CN or NaBH(OAc)$_3$ in a one-step procedure in a solvent like methanol or ethanol preferably around room temperature to reflux temperature (Scheme 2, step d). Alternatively, the reaction can be conducted in a two-step procedure by first treatment with suitable amines, e.g. ammonia in methanol and titanium (IV) isopropoxide with no additional solvent between 0° C. and room temperature or in solvents like methanol or toluene preferably at temperatures between room temperature and the reflux temperature of the solvents and the subsequent addition of the reducing agent such NaBH$_4$ preferably between 0° C. and room temperature. Further, ketone intermediates 4a can be transformed to the corresponding hydroxyl compounds 5 ($R^{12}$ is H) with hydride reducing agents such as BH$_3$ or NaBH$_4$ (e.g. in methanol around room temperature; Scheme 2, step e) or by using aluminium reducing agents such as LiAlH$_4$. Enantiomers or diastereoisomers produced during this reaction can be separated by methods known to the man skilled in the art such as e.g. chiral chromatography or crystallization. In the presence of appropriate chiral ligands (e.g. chiral oxazaborolidines, E. J. Corey, R. K. Bakshi, S. Shibata, *J. Am. Chem. Soc.* 1987, 109, 5551) the reaction can also be conducted in an enantioselective fashion providing access to a single enantiomer in high enantiomeric excess (typically ee>95%). Alternatively, asymmetric reductions of 4a can also be achieved by biocatalysis utilizing reductases in the presence of appropriate reducing agents (e.g. baker's yeast; for a review see: K. Nakamura, R. Yamanaka, T. Matsuda, T. Harada, *Tetrahedron Asym.* 2003, 14, 2659). Reaction of ketones 4a with Grignard reagents $R^{12}$MgX (X=halogen, $R^{12}$ is different from H) or with a lithium reagent $R^{12}$Li ($R^{12}$ is different from H) in solvents like THF or diethyl ether in the presence of lithium salts such as lithium chloride and a temperature range between −78° C. to room temperature provides access to compounds 5 by methods well known in the art (Scheme 2, step e). Compounds 5 and 6 can be purified by classical means such as silica column chromatography, MPLC or preparative HPLC providing racemates or diatereomeric mixtures. Enantiomers or diastereoisomers produced during this reaction can be obtained by methods known to the man skilled in the art such as e.g. chiral chromatography or crystallization.

Scheme 2

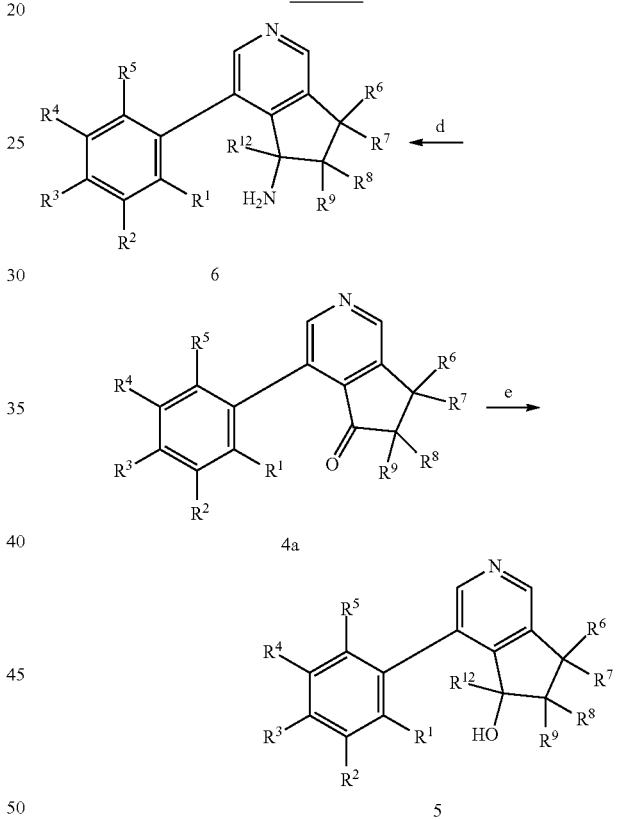

Carboxylic acids of general structure 7 can be prepared by Kondrat'eva reaction from 2-cyclopent-2-en-1-ylacetic acid (compound of type 2 wherein B is —(CR$^{14}$R$^{15}$)$_p$—COOH) and the corresponding aryl oxazoles 1 as outlined in Scheme 1 (step a). Amide compounds 8 are formed by amide coupling reactions between compounds 8 and primary or secondary amines (HNR$^{16}$R$^{17}$) using well known coupling methods like e.g. using EDCI optionally in the presence of HOBT or DMAP and a base like Huenig's base (N,N-diisopropylethylamine) in solvents like N,N-dimethylformamide preferably between 0° C. and room temperature or by use of HATU or TBTU and triethylamine or N,N-diisopropylethylamine in N,N-dimethylformamide preferably between 0° C. and room temperature (Scheme 3, step f). Carboxylic esters of structure 9 are accessible via refluxing of the parent carboxylic acid 7 with the appropriate alcohol (e.g. methanol, ethanol, isopropanol) in the presence of an acid catalyst such as sulfuric acid, p-toluene sulfonic acid or Amberlite ion exchange resins (Scheme 3, step g). Alternative esterification reactions of carboxylic acids 7 with alcohols employ coupling reagents such as HATU or TBTU in the presence of an amine base like Huenig's base or triethylamine in solvents like DMF preferably between 0° C. and room temperature. Alternatively, the use of DCC or EDCI in the presence of DMAP or carboxylic acid chlorides or anhydrides can be employed, all methods well known to persons skilled in the art. Esterification of carboxylic acids 7 can also be conducted with alkylating agents such as methyl iodide, ethyl iodide, ethyl bromide or dimethyl sulfate in the presence of a base such as potassium or sodium carbonate or amine base like DBU in a solvent such as acetone or THF. Amide compounds 8 are also accessible from carboxylic esters 9 by treatment with trimethylaluminium (TMA) in the presence of the reacting amine in a solvent like toluene or THF preferably in a temperature range between 0° C. and room temperature (Scheme 3, step h). Compounds 9 can be converted into amino compounds 10 via formation of the corresponding primary amides (Scheme 3, step i, e.g. by amide formation with ammonia in a suitable solvent as methanol, or by saponification followed by standard amide coupling with ammonia) followed by a Hofmann rearrangement: treatment with sodium hydroxide and bromine in a solvent like ethanol preferably between about 0° C. and the reflux temperature of the solvent (Scheme 3, step j).

Alternatively, ester compounds 9 can be converted into ketones 13 (Scheme 5), wherein $R^{14a}$ is alkyl, haloalkyl, cycloalkyl or halocycloalkyl, via Weinreb amides: hydrolysis of ester 9 (step 1), transformation into methoxy-N-methyl-amides (step m) followed by reaction with Grignard reagents $R^{14a}MgX$ or lithium reagents $R^{14a}Li$ in solvents like THF in a temperature range between −78° C. and room temperature (step n) provides ketones 13. Compounds 13 can react with a hydride reducing agent like sodium borohydride (e.g. in methanol around room temperature) or with a Grignard reagent $R^{15a}MgX$ or with a lithium reagent $R^{15a}Li$ in solvents like THF in a temperature range between −78° C. to give compounds 14 by methods well known in the art (step o). The hydroxy substituent in 14 can be converted into a leaving group such as halogen, tosylate, mesylate or triflate by method known in the art (step p) and subsequently reacted with amino compounds 15, optionally in the presence of a base like Huenig's base or sodium hydride in solvents like DMF, DMA or 1-methyl-2-pyrrolidone in a temperature range between 0° C. and about 100° C. to give substituted amino compounds 16 (step q). $R^{16}$ and $R^{17}$ can be modified further as described in Scheme 4 to give the final compounds of formula (I).

Building blocks 14 (Scheme 5, step r) can further be transformed to ethers 17, wherein $R^{16}$ is alkyl, haloalkyl, cycloalkyl, hydroxyalkyl, alkoxyalkyl or haloalkoxyalkyl, using corresponding $R^{16}$-halides, $R^{16}$-mesylates or $R^{16}$-tosylates in the presence of a base like sodium hydride or after anion formation e.g. with sodium hydride in solvents like DMF, DMA or 1-methyl-2-pyrrolidone in a temperature range between 0° C. and about 100° C.

Scheme 5

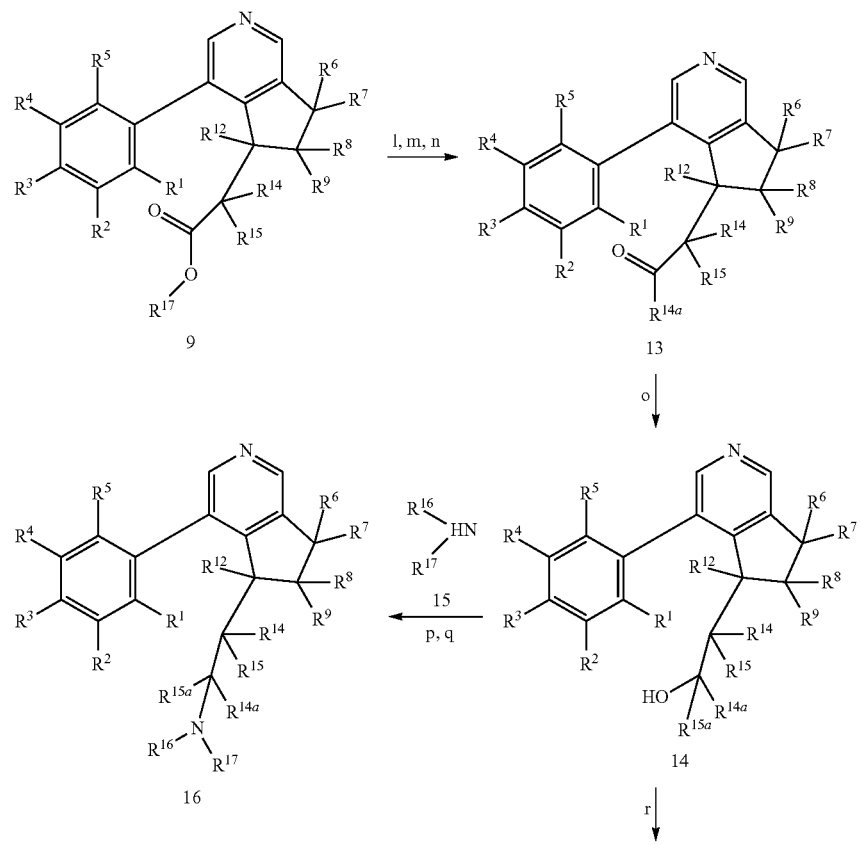

-continued

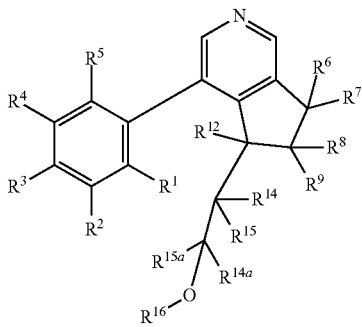

Also an embodiment of the present invention is a process to prepare a compound of formula (I) as defined above comprising the reaction of a compound of formula (II) in the presence of a compound of formula (III);

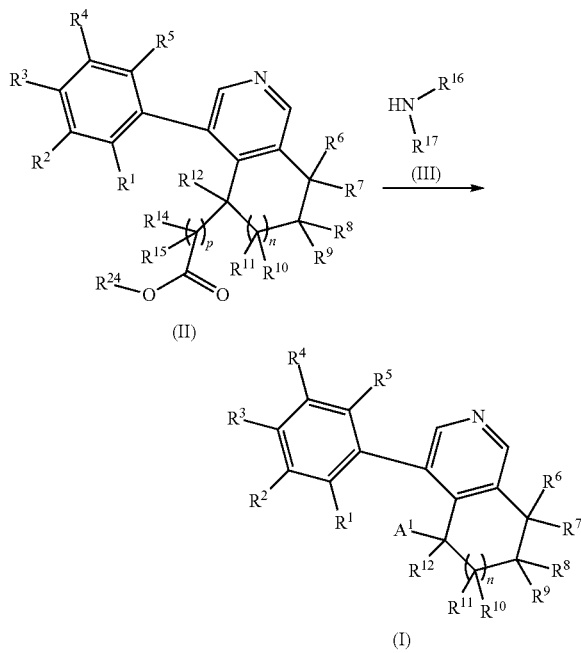

wherein $R^1$, $R^2$, $R^3$, $R^4$, $R^5$, $R^6$, $R^7$, $R^8$, $R^9$, $R^{10}$, $R^{11}$, $R^{12}$, $R^{14}$, $R^{15}$, $R^{16}$, $R^{17}$, n and p are as defined herein, $R^{24}$ is alkyl and $A^1$ is —$(CR^{14}R^{15})_p$—C(O)$NR^{16}R^{17}$.

In particular, in the presence of EDCI and optionally in the presence of HOBT or DMAP and a base like Huenig's base (N,N-diisopropylethylamine) in solvents like N,N-dimethylformamide preferably between 0° C. and room temperature or by use of HATU or TBTU and triethylamine or N,N-diisopropylethylamine in N,N-dimethylformamide preferably between 0° C. and room temperature.

Also an object of the present invention is a compound according to formula (I) as described herein for use as therapeutically active substance.

Likewise an object of the present invention is a pharmaceutical composition comprising a compound according to formula (I) as described herein and a therapeutically inert carrier.

The present invention also relates to the use of a compound according to formula (I) as described herein for the treatment or prophylaxis of chronic kidney disease, congestive heart failure, hypertension, primary aldosteronism and Cushing syndrome.

The present invention also relates to the use of a compound according to formula (I) as described herein for the treatment or prophylaxis of diabetic nephropathy.

The present invention also relates to the use of a compound according to formula (I) as described herein for the treatment or prophylaxis of kidney or heart fibrosis.

The present invention also relates to the use of a compound according to formula (I) as described herein for the treatment or prophylaxis of chronic kidney disease.

The present invention also relates to the use of a compound according to formula (I) as described herein for the treatment or prophylaxis of congestive heart failure.

The present invention also relates to the use of a compound according to formula (I) as described herein for the treatment or prophylaxis of hypertension.

The present invention also relates to the use of a compound according to formula (I) as described herein for the treatment or prophylaxis of primary aldosteronism.

A particular embodiment of the present invention is a compound according to formula (I) as described herein for the treatment or prophylaxis of chronic kidney disease, congestive heart failure, hypertension, primary aldosteronism and Cushing syndrome.

Also a particular embodiment of the present invention is a compound according to formula (I) as described herein for the treatment or prophylaxis of diabetic nephropathy.

Another particular embodiment of the present invention is a compound according to formula (I) as described herein for the treatment or prophylaxis of kidney or heart fibrosis.

Also a particular embodiment of the present invention is a compound according to formula (I) as described herein for the treatment or prophylaxis of chronic kidney disease.

Also a particular embodiment of the present invention is a compound according to formula (I) as described herein for the treatment or prophylaxis of congestive heart failure.

Also a particular embodiment of the present invention is a compound according to formula (I) as described herein for the treatment or prophylaxis of hypertension.

Also a particular embodiment of the present invention is a compound according to formula (I) as described herein for the treatment or prophylaxis of primary aldosteronism.

The present invention also relates to the use of a compound according to formula (I) as described herein for the preparation of a medicament for the treatment or prophylaxis of chronic kidney disease, congestive heart failure, hypertension, primary aldosteronism and Cushing syndrome.

The present invention also relates to the use of a compound according to formula (I) as described herein for the preparation of a medicament for the treatment or prophylaxis of diabetic nephropathy.

The present invention also relates to the use of a compound according to formula (I) as described herein for the preparation of a medicament for the treatment or prophylaxis of kidney or heart fibrosis.

Also an embodiment of the present invention is the use of a compound according to formula (I) as described herein for the preparation of a medicament for the treatment or prophylaxis of chronic kidney disease.

Also an embodiment of the present invention is the use of a compound according to formula (I) as described herein for the preparation of a medicament for the treatment or prophylaxis of congestive heart failure.

Also an embodiment of the present invention is the use of a compound according to formula (I) as described herein for the preparation of a medicament for the treatment or prophylaxis of hypertension.

Also an embodiment of the present invention is the use of a compound according to formula (I) as described herein for the preparation of a medicament for the treatment or prophylaxis of primary aldosteronism.

Also an object of the invention is a method for the treatment or prophylaxis of chronic kidney disease, congestive heart failure, hypertension, primary aldosteronism and Cushing syndrome, which method comprises administering an effective amount of a compound according to formula (I) as described herein.

Also an object of the invention is a method for the treatment or prophylaxis of diabetic nephropathy, which method comprises administering an effective amount of a compound according to formula (I) as described herein.

Also an object of the invention is a method for the treatment or prophylaxis of kidney or heart fibrosis, which method comprises administering an effective amount of a compound according to formula (I) as described herein.

Also an embodiment of the present invention is a method for the treatment or prophylaxis of chronic kidney disease, which method comprises administering an effective amount of a compound according to formula (I) as described herein.

Also an embodiment of the present invention is a method for the treatment or prophylaxis of congestive heart failure, which method comprises administering an effective amount of a compound according to formula (I) as described herein.

Also an embodiment of the present invention is a method for the treatment or prophylaxis of hypertension, which method comprises administering an effective amount of a compound according to formula (I) as described herein.

Also an embodiment of the present invention is a method for the treatment or prophylaxis of primary aldosteronism, which method comprises administering an effective amount of a compound according to formula (I) as described herein.

Also an embodiment of the present invention is a compound of formula (I) as described herein, when manufactured according to any one of the described processes.

ASSAY PROCEDURES

Herein we identified the use of the G-402 cell line as a host cell to ectopically express (transiently or stably) enzymes of the CYP11 family. Specifically we developed stable G-402 cells expressing ectopically human CYP11B1, human CYP11B2, human CYP11A1, cynmolgus CYP11B1 or cynomolgus CYP11B2 enzyme activity. Importantly the identified cell line G-402 expresses co-factors (adrenodoxin and adrenodoxin reductase) important for the activity of the CYP11 family and no relevant enzyme activity of the CYP11 family (in comparison to H295R cells) was detected in these cells. Therefore the G-402 cell line is uniquely suited as a host cell for the ectopic expression of enzymes from the CYP11 family. G-402 cells can be obtained from ATCC (CRL-1440) and were originally derived from a renal leiomyoblastoma.

The expression plasmids contains the ORF for either human/cyno CYP11B1 or CYP11B2 under the control of a suitable promoter (CMV-promoter) and a suitable resistance marker (neomycin). Using standard techniques the expression plasmid is transfected into G-402 cells and these cells are then selected for expressing the given resistance markers. Individual cell-clones are then selected and assessed for displaying the desired enzymatic activity using 11-Deoxycorticosterone (Cyp11B2) or 11-Deoxycortisol (Cyp11B1) as a substrate.

G-402 cells expressing CYP11 constructs were established as described above and maintained in McCoy's 5a Medium Modified, ATCC Catalog No. 30-2007 containing 10% FCS and 400 µg/ml G418 (Geneticin) at 37° C. under an atmosphere of 5% CO2/95% air. Cellular enzyme assays were performed in DMEM/F12 medium containing 2.5% charcoal treated FCS and appropriate concentration of substrate (0.3-10 uM 11-Deoxycorticosterone, 11-Deoxycortisol or Corticosterone). For assaying enzymatic activity, cells were plated onto 96 well plates and incubated for 16 h. An aliquot of the supernatant is then transferred and analyzed for the concentration of the expected product (Aldosterone for CYP11B2; Cortisol for CYP11B1). The concentrations of these steroids can be determined using HTRF assays from CisBio analyzing either Aldosterone or Cortisol.

Inhibition of the release of produced steroids can be used as a measure of the respective enzyme inhibition by test compounds added during the cellular enzyme assay. The dose dependent inhibition of enzymatic activity by a compound is calculated by means of plotting added inhibitor concentrations (x-axes) vs. measured steroid/product level (y-axes). The inhibition is then calculated by fitting the following 4-parameter sigmoidal function (Morgan-Mercer-Flodin (MMF) model) to the raw data points using the least squares method:

$$y = \frac{AB + Cx^D}{B + x^D}$$

wherein, A is the maximum y value, B is the EC50 factor determined using XLFit, C is the minimum y value and D is the slope value.

The maximum value A corresponds to the amount of steroid produced in the absence of an inhibitor, the value C corresponds to the amount of steroid detected when the enzyme is fully inhibited.

EC50 values for compounds claimed herein were tested with the G402-based assay system described. Cyp11B2 enzyme activity was tested in presence of 1 µM Deoxycorticosterone and variable amounts of inhibitors; Cyp11B1 enzyme activity was tested in presence of 1 µM Deoxycortisol and variable amounts of inhibitors.

| Example | EC50 human CYP11B1 μM | EC50 human CYP11B2 μM |
|---------|-----------------------|-----------------------|
| 1 | 5.346 | 0.263 |
| 2 | 2.341 | 0.069 |
| 3 | 2.336 | 0.045 |
| 4 | 1.958 | 0.050 |
| 5 | 3.331 | 0.133 |
| 6 | >30 | 0.739 |
| 7 | 14.422 | 0.740 |
| 8 | 7.385 | 0.033 |
| 9 | 34.956 | 0.742 |
| 10 | 8.131 | 0.063 |
| 11 | 0.367 | 0.064 |
| 12 | 1.031 | 0.113 |
| 13 | 1.153 | 0.060 |
| 14 | 2.604 | 1.531 |
| 15 | >30 | 0.832 |
| 16 | 3.628 | 1.021 |
| 17 | 0.311 | 0.100 |
| 18 | 0.282 | 0.597 |
| 19 | 8.474 | 0.442 |
| 20 | 6.004 | 0.213 |
| 21 | 8.358 | 0.413 |
| 22 | 9.445 | 0.957 |
| 23 | 8.610 | 0.487 |
| 24 | 3.966 | 0.205 |

Compounds of formula (I) and their pharmaceutically acceptable salts or esters thereof as described herein have $EC_{50}$ (CYP11B2) values between 0.000001 uM and 1000 uM, particular compounds have $EC_{50}$ (CYP11B2) values between 0.00005 uM and 500 uM, further particular compounds have $EC_{50}$ (CYP11B2) values between 0.0005 uM and 50 uM, more particular compounds have $EC_{50}$ (CYP11B2) values between 0.0005 uM and 5 uM. These results have been obtained by using the described enzymatic assay.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

In accordance with the invention, the compounds of formula (I) or their pharmaceutically acceptable salts and esters can be used for the treatment or prophylaxis of aldosterone mediated diseases.

The compounds of formula (I) or their pharmaceutically acceptable salts and esters herein are inhibitiors of CYP11B2. The compounds of formula (I) or their pharmaceutically acceptable salts and esters herein display also variable inhibition of CYP11B1 but present an improved selectivity towards CYP11B2 versus CYP11B1. Such compounds may be used for treatment or prophylaxis of conditions displaying excessive cortisol production/levels or both excessive cortisol and aldosterone levels (for ex. Cushing syndrome, burn trauma patients, depression, post-traumatic stress disorders, chronic stress, corticotrophic adenomas, Morbus Cushing).

In accordance with the invention, the compounds of formula (I) or their pharmaceutically acceptable salts and esters can be used for the treatment or prophylaxis of cardiovascular conditions (including hypertension and heart failure), vascular conditions, endothelial dysfunction, baroreceptor dysfunction, renal conditions, liver conditions, fibrotic diseases, inflammatory conditions, retinopathy, neuropathy (such as peripheral neuropathy), pain, insulinopathy, edema, edematous conditions, depression and the like.

Cardiovascular conditions include congestive heart failure, coronary heart disease, arrhythmia, arterial fibrillation, cardiac lesions, decreased ejection fraction, diastolic and systolic heart dysfunction, fibrinoid necrosis of coronary arteries, cardiac fibrosis, hypertrophic cardiomyopathy, impaired arterial compliance, impaired diastolic filling, ischemia, left ventricular hypertrophy, myocardial and vascular fibrosis, myocardial infarction, myocardial necrotic lesions, cardiac arrhythmias, prevention of sudden cardiac death, restenosis, stroke, vascular damage.

Renal conditions include acute and chronic renal failure, nephropathy, end-stage renal disease, diabetic nephropathy, decreased creatinine clearance, decreased glomerular filtration rate, expansion of reticulated mesangial matrix with or without significant hypercellularity, focal thrombosis of glomerular capillaries, global fibrinoid necrosis, glomerulosclerosis, ischemic lesions, malignant nephrosclerosis (such as ischemic retraction, microalbuminuria, proteinuria, reduced renal blood flow, renal arteriopathy, swelling and proliferation of intracapillary (endothelial and mesangial) and/or extracapillary cells (crescents).

Renal conditions also include glomerulonephritis (such as diffuse proliferative, focal proliferative, mesangial proliferative, membranoproliferative, minimal change membranous glomerulonephritis), lupus nephritis, non-immune basement membrane abnormalities (such as Alport syndrome), renal fibrosis and glomerulosclerosis (such as nodular or global and focal segmental glomerulosclerosis).

Liver conditions include, but are not limited to, liver steatosis, nonalcoholic steatohepatitis, liver cirrhosis, liver ascites, hepatic congestion and the like.

Vascular conditions include, but are not limited to, thrombotic vascular disease (such as mural fibrinoid necrosis, extravasation and fragmentation of red blood cells, and luminal and/or mural thrombosis), proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction, and the like.

Inflammatory conditions include, but are not limited to, arthritis (for example, osteoarthritis), inflammatory airways diseases (for example, chronic obstructive pulmonary disease (COPD)), and the like.

Pain includes, but is not limited to, acute pain, chronic pain (for example, arthralgia), and the like.

Edema includes, but is not limited to, peripheral tissue edema, hepatic congestion, liver ascites, splenic congestion, respiratory or lung congestion, and the like.

Insulinopathies include, but are not limited to, insulin resistance, Type I diabetes mellitus, Type II diabetes mellitus, glucose sensitivity, pre-diabetic state, pre-diabetes, syndrome X, and the like.

Fibrotic diseases include, but are not limited to myocardial and intrarenal fibrosis, renal interstitial fibrosis and liver fibrosis.

Furthermore, the compounds of formula (I) or their pharmaceutically acceptable salts and esters as described herein can also be used for the treatment or prophylaxis of cardiovascular condition selected from the group consisting of hypertension, heart failure (particularly heart failure post myocardial infarction), left ventricular hypertrophy, and stroke.

In another embodiment, the cardiovascular condition is hypertension.

In particular embodiment, the cardiovascular condition is treatment-resistant hypertension.

In another embodiment, the cardiovascular condition is heart failure.

In another embodiment, the cardiovascular condition is left ventricular hypertrophy.

In another embodiment, the cardiovascular condition is congestive heart failure, more particularly in patients with preserved left ventricular ejection fraction.

In another embodiment, the cardiovascular condition is stroke.

In another embodiment, the compounds of formula (I) or their pharmaceutically acceptable salts and esters can be used for the treatment or prophylaxis renal condition.

In another embodiment, the renal condition is nephropathy.

In another embodiment, the renal condition is auto-immune glomerulonephritis.

In another embodiment, the chronic kidney disease is diabetic nephropathy.

In another embodiment, the fibrotic disease is kidney or heart fibrosis.

In another embodiment, the compounds of formula (I) or their pharmaceutically acceptable salts and esters can be used for the treatment or prophylaxis Type II diabetes mellitus.

In another embodiment, the compounds of formula (I) or their pharmaceutically acceptable salts and esters can be used for the treatment or prophylaxis Type I diabetes mellitus.

In another embodiment, the compounds of formula (I) or their pharmaceutically acceptable salts and esters can be used for the treatment or prophylaxis of diabetic retinopathy.

The invention is illustrated hereinafter by Examples, which have no limiting character.

In case the preparative examples are obtained as a mixture of enantiomers, the pure enantiomers can be separated by methods described herein or by methods known to the persons skilled in the art, such as e.g. chiral chromatography or crystallization.

EXAMPLES

Intermediate A-1

4-[3-Fluoro-4-(trifluoromethyl)phenyl]-6,7-dihydro-cyclopenta[c]pyridin-5-one

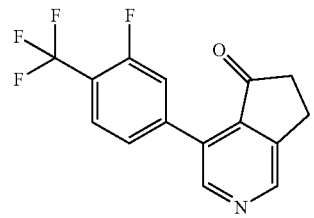 [SMILES: O=C1CCc2cncc(-c3ccc(C(F)(F)F)c(F)c3)c21]

[A]5-[3-Fluoro-4-(trifluoromethyl)phenyl]oxazole

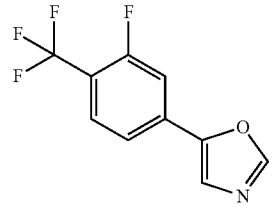 [SMILES: Fc1cc(-c2cnco2)ccc1C(F)(F)F]

A solution of 3-fluoro-4-(trifluoromethyl)benzaldehyde (1.40 g, 7.07 mmol) and p-toluenesulfonylmethyl isocyanide (1.53 g, 7.68 mmol; TosMIC) in MeOH (100 mL) was treated with potassium carbonate (1.97 g, 14.14 mmol) and the suspension heated to reflux for 14 h. After being cooled to room temperature, the solvent was removed under reduced pressure and the crude product triturated with water at 0° C. (2×25 mL). The slightly orange precipitate was collected by filtration and dried under vacuum (4.46 g, 92%). MS: 232.0 (M+H)$^+$.

[B]4-[3-Fluoro-4-(trifluoromethyl)phenyl]-6,7-di-hydro-5H-cyclopenta[c]pyridine

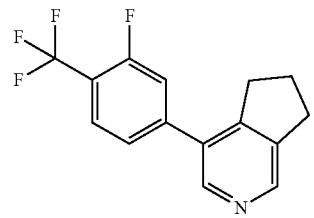 [SMILES: Fc1cc(-c2cncc3c2CCC3)ccc1C(F)(F)F]

A solution of 5-[3-fluoro-4-(trifluoromethyl)phenyl]oxazole (0.50 g, 2.16 mmol), cyclopentene (2.95 g, 43.3 mmol) and trifluoroacetic acid (0.49 g, 4.33 mmol) in o-dichlorobenzene (12 mL) was heated under microwave irradiation to 220° C. for 6 h. To the reaction mixture was added triethylamine (5 mL) and the solvent mixture removed under reduced pressure. Purification by MPLC (70 g SiO₂, Telos-cartridge) eluting with a 0 to 50% EtOAc-n-heptane gradient provided the title compound (0.27 g, 44%) as a slightly brown solid. MS: 282.5 (M+H)⁺.

Alternatively, this reaction step has also been conducted under flow conditions:

The reaction was performed on a custom-made flow system consisting of a Dionex P580 pump and a HP 6890 Series Gas Chromatography oven used as a heating source. The GC oven was equipped with a stainless steel coil reactor (53 mL volume) made from Supelco stainless steel tube (ID=2.1 mm). After heating to 230° C. using toluene as a system solvent, a mixture of cyclopentene (1.77 g, 26.0 mmol) and trifluoroacetic acid (0.30 g, 2.60 mmol) in toluene (1.0 mL), a mixture of 5-[3-fluoro-4-(trifluoromethyl)phenyl]oxazole (0.30 g, 1.30 mmol), cyclopentene (1.77 g, 26.0 mmol) and trifluoroacetic acid (0.30 g, 2.60 mmol) in toluene (1.0 mL) and finally a mixture of cyclopentene (1.77 g, 26.0 mmol) and trifluoroacetic acid (0.30 g, 2.60 mmol) in toluene (1.0 mL) were injected onto the stainless steel coil reactor in sequential order. The system was run at a flow rate of 0.35 mL/min equaling to a nominal residence time of $t_R$=150 min and an effective residence time of $t_{R,eff}$=120 min taking the 25% volume expansion of toluene at 230° C. into account (R. E. Martin et al., *Eur. J. Org. Chem.* 2012, 47-52). A 750 psi back-pressure regulator with a protection guard (filled with sand/glass wool) was used at the exit of the reactor to maintain system pressure. The reaction mixture was collected in a round bottom flask, triethylamine (5 mL) was added and the solvent mixture removed under reduced pressure. Purification by MPLC (50 g SiO₂, Telos-cartridge) eluting with a 0 to 50% EtOAc-n-heptane gradient provided the title compound (0.18 g, 50%) as a slightly brown solid. MS: 282.5 (M+H)⁺.

[C]4-[3-Fluoro-4-(trifluoromethyl)phenyl]-6,7-dihydrocyclopenta[c]pyridin-5-one

Intermediate A-1

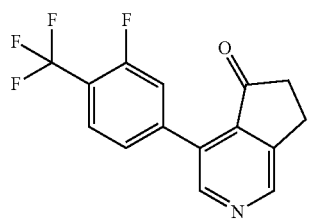 [SMILES: O=C1CCc2cncc(-c3ccc(C(F)(F)F)c(F)c3)c21]

To a solution of 4-[3-fluoro-4-(trifluoromethyl)phenyl]-6,7-dihydro-5H-cyclopenta[c]pyridine (76.0 mg, 0.27 mmol) and dirhodium(II, III) tetrakis caprolactamate (1.8 mg, 0.0027 mmol; synthesis described in M. P. Doyle et al., *J. Am. Chem. Soc.* 1993, 115, 958-964) in DCM (0.5 mL) was added sodium bicarbonate (22.7 mg, 0.27 mmol) and tert-butyl hydroperoxide (0.25 mL, 1.35 mmol). The reaction mixture was stirred at room temperature for 48 h. During this time period additional equivalents of tert-butyl hydroperoxide (1.25 mL, 6.75 mmol) were added in small portions. The solvent was removed under reduced pressure and the crude reaction mixture purified by MPLC (20 g SiO₂, Telos-cartridge) eluting with a 0 to 50% EtOAc-n-heptane gradient to provide 4-[3-fluoro-4-(trifluoromethyl)phenyl]-5,6-dihydrocyclopenta[c]pyridin-7-one [15.5 mg, 19%; MS: 296.1 (M+H)⁺] and the title compound [17.4 mg, 22%; MS: 296.4 (M+H)⁺] both as slightly yellow solids.

Intermediate A-2

4-[2-Fluoro-4-(trifluoromethyl)phenyl]-6,7-dihydrocyclopenta[c]pyridin-5-one

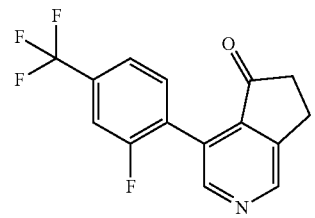 [SMILES: O=C1CCc2cncc(-c3ccc(C(F)(F)F)cc3F)c21]

[A]4-[2-Fluoro-4-(trifluoromethyl)phenyl]-6,7-dihydro-5H-cyclopenta[c]pyridine

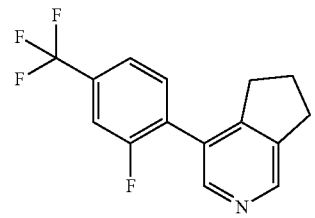 [SMILES: Fc1cc(C(F)(F)F)ccc1-c1cncc2c1CCC2]

In analogy to the procedure described for the preparation of 4-[3-fluoro-4-(trifluoromethyl)phenyl]-6,7-dihydro-5H-cyclopenta[c]pyridine (intermediate A-1, step B, flow approach), replacing 5-[3-fluoro-4-(trifluoromethyl)phenyl]oxazole with 5-[2-fluoro-4-(trifluoromethyl)phenyl]oxazole (CAS[1146694-91-8]). The flow process was run at 250° C. with an effective residence time of $t_{R,eff}$=120 min. The title compound was obtained as a light brown solid (54%). MS: 282.1 (M+H)⁺.

[B]4-[2-Fluoro-4-(trifluoromethyl)phenyl]-6,7-dihydrocyclopenta[c]pyridin-5-one

Intermediate A-2

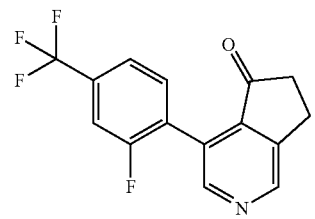 [SMILES: O=C1CCc2cncc(-c3ccc(C(F)(F)F)cc3F)c21]

In analogy to the procedure described for the preparation of 4-[3-fluoro-4-(trifluoromethyl)phenyl]-6,7-dihydrocyclopenta[c]pyridin-5-one (intermediate A-1) and 4-[3-fluoro-4-(trifluoromethyl)phenyl]-5,6-dihydrocyclopenta[c]pyridin-7-one (intermediate A-2), replacing 4-[3-fluoro-4-(trifluoromethyl)phenyl]-6,7-dihydro-5H-cyclopenta[c]pyridine with 4-[2-fluoro-4-(trifluoromethyl)phenyl]-6,7-dihydro-5H-cyclopenta[c]pyridine. The title compound [20%; MS: 296.1 (M+H)$^+$] and 4-[2-fluoro-4-(trifluoromethyl)phenyl]-5,6-dihydrocyclopenta[c]pyridin-7-one [30%; MS: 296.1 (M+H)$^+$] were obtained as off-white solids.

Intermediate A-3

(rac)-2-[4-[3-Fluoro-4-(trifluoromethyl)phenyl]-6,7-dihydro-5H-cyclopenta[c]pyridin-5-yl]acetic acid and (rac)-2-[4-[3-Fluoro-4-(trifluoromethyl)phenyl]-6,7-dihydro-5H-cyclopenta[c]pyridin-7-yl]acetic acid Intermediate A-3

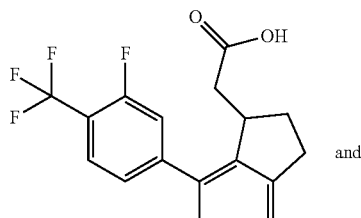

and

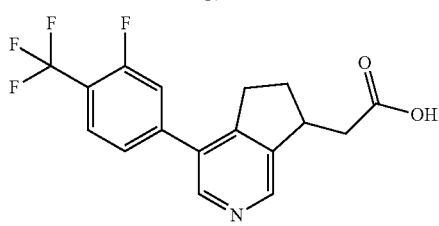

In analogy to the procedure described for the preparation of 4-[3-fluoro-4-(trifluoromethyl)phenyl]-6,7-dihydro-5H-cyclopenta[c]pyridine (intermediate A-1, step B, batch approach), replacing cyclopentene with 2-cyclopent-2-en-1-ylacetic acid (CAS[13668-61-6]). The reaction was conducted neat and heated under microwave irradiation to 180° C. for 17 h. After purification by MPLC (70 g SiO$_2$, Telos-cartridge) eluting with a 0 to 100% EtOAc-n-heptane gradient the title compounds were obtained as slightly brown oil (36%; approximate 1:1 mixture). MS: 340.2 (M+H)$^+$ (2-[4-[3-fluoro-4-(trifluoromethyl)phenyl]-6,7-dihydro-5H-cyclopenta[c]pyridin-5-yl]acetic acid) and MS: 340.2 (M+H)$^+$ (2-[4-[3-fluoro-4-(trifluoromethyl)phenyl]-6,7-dihydro-5H-cyclopenta[c]pyridin-7-yl]acetic acid). The subsequent reactions were conducted without further separation of the two regioisomers.

Intermediate A-4

(rac)-2-[4-[2-Fluoro-4-(trifluoromethyl)phenyl]-6,7-dihydro-5H-cyclopenta[c]pyridin-5-yl]acetic acid and (rac)-2-[4-[2-Fluoro-4-(trifluoromethyl)phenyl]-6,7-dihydro-5H-cyclopenta[c]pyridin-7-yl]acetic acid Intermediate A-4

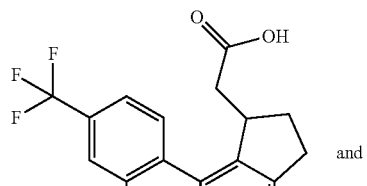

and

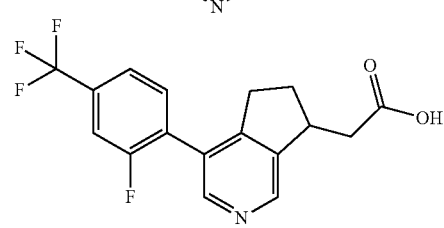

In analogy to the procedure described for the preparation of 4-[3-fluoro-4-(trifluoromethyl)phenyl]-6,7-dihydro-5H-cyclopenta[c]pyridine (intermediate A-1, step B, batch approach), replacing cyclopentene with 2-cyclopent-2-en-1-ylacetic acid (CAS[13668-61-6]). The reaction was conducted neat and heated under microwave irradiation to 200° C. for 10 h. After purification by MPLC (70 g SiO$_2$, Telos-cartridge) eluting with a 0 to 100% EtOAc-n-heptane gradient the title compounds were obtained as slightly brown oil (34%; approximate 1:1 mixture). MS: 340.5 (M+H)$^+$ (2-[4-[2-fluoro-4-(trifluoromethyl)phenyl]-6,7-dihydro-5H-cyclopenta[c]pyridin-5-yl]acetic acid) and MS: 340.5 (M+H)$^+$ (2-[4-[2-fluoro-4-(trifluoromethyl)phenyl]-6,7-dihydro-5H-cyclopenta[c]pyridin-7-yl]acetic acid). The subsequent reactions were conducted without further separation of the two regioisomers.

Example 1

(rac)-4-(3-Fluoro-4-(trifluoromethyl)phenyl)-6,7-dihydro-5H-cyclopenta[c]pyridin-5-amine

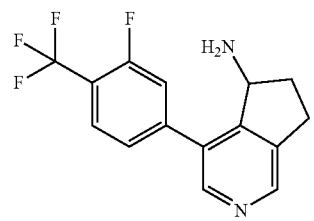 [SMILES: NC1CCc2cncc(-c3ccc(C(F)(F)F)c(F)c3)c21]

A solution of ammonium acetate (1.57 g, 20.4 mmol) in MeOH (7 mL) was treated with 4-[2-fluoro-4-(trifluoromethyl)phenyl]-6,7-dihydrocyclopenta[c]pyridin-5-one (intermediate A-1) (0.20 g, 0.68 mmol) and the reaction mixture stirred at room temperature for 1 h. Sodium cyanoborohydride (0.15 g, 2.39 mmol) was added and stirring continued at room temperature. After 15 min, the reaction mixture was heated to reflux for 90 min. The solvent was removed under reduced pressure, a sat. aq. solution of ammonium chloride (2 mL) and a 1 M solution of HCl (2 mL) were added and the aq. phase washed with DCM (3×5 mL). To the aq. phase was added a 1 M solution of NaOH (4 mL) and extracted with DCM (3×5 mL). The combined organic phases were dried over MgSO₄ and concentrated under reduced pressure. The title compound was isolated as light brown solid (74 mg, 37%). MS: 297.4 (M+H)⁺.

Example 2

(rac)-4-(3-Fluoro-4-(trifluoromethyl)phenyl)-6,7-dihydro-5H-cyclopenta[c]pyridin-5-ol

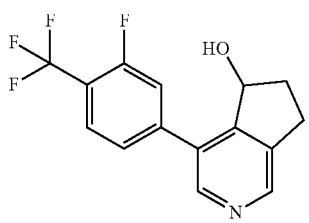 [SMILES: OC1CCc2cncc(-c3ccc(C(F)(F)F)c(F)c3)c21]

A solution of 4-(3-fluoro-4-trifluoromethyl-phenyl)-6,7-dihydro-[2]pyrindin-5-one (intermediate A-1) (15.9 mg, 0.054 mmol) in methanol (1 mL) was treated at 0° C. with sodium borohydride (2.0 mg, 0.954 mmol). After 10 min, the reaction mixture was quenched by addition of acetic acid (0.43 mL) and the crude reaction mixture concentrated under reduced pressure. A sat. aq. solution of sodium bicarbonate (5 mL) was added and the aq. phase extracted with EtOAc (3×10 mL). The combined organic phases were dried over Na₂SO₄ and concentrated under reduced pressure. Purification by MPLC eluting with a gradient of DCM-isopropanol provided the title compound as off-white solid (14 mg, 88%). MS: 298.1 (M+H)⁺.

Example 3

(rac)-4-(3-Fluoro-4-(trifluoromethyl)phenyl)-5-methyl-6,7-dihydro-5H-cyclopenta[c]pyridin-5-ol

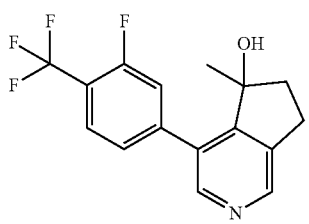 [SMILES: CC1(O)CCc2cncc(-c3ccc(C(F)(F)F)c(F)c3)c21]

A solution of 4-(3-fluoro-4-trifluoromethyl-phenyl)-6,7-dihydro-[2]pyrindin-5-one (intermediate A-1) (25 mg, 0.085 mmol) and lithium chloride (10.9 mg, 0.25 mmol) in diethyl ether (3 mL) under argon was treated with methyllithium (0.063 mL, 0.10 mmol; 1.6 M solution in diethyl ether) and the reaction mixture stirred at 0° C. After 1 h stirring was continued at room temperature for 3 h. The reaction mixture was quenched by addition of a sat. aq. solution of ammonium chloride (10 mL) and the aq. phase extracted with EtOAc (3×10 mL). The combined organic phases were dried over MgSO₄ and concentrated under reduced pressure. Purification by preparative HPLC on reversed phase eluting with a gradient of acetonitrile-water provided the title compound as off-white solid (12 mg, 46%). MS: 312.1 (M+H)⁺.

Example 4

(rac)-4-(3-Fluoro-4-(trifluoromethyl)phenyl)-5-phenyl-6,7-dihydro-5H-cyclopenta[c]pyridin-5-ol

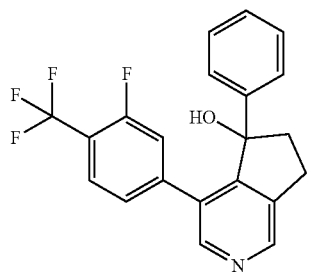 [SMILES: OC1(c2ccccc2)CCc2cncc(-c3ccc(C(F)(F)F)c(F)c3)c21]

A solution of 4-(3-fluoro-4-trifluoromethyl-phenyl)-6,7-dihydro-[2]pyrindin-5-one (intermediate A-1) (25 mg, 0.085 mmol) and lithium chloride (10.9 mg, 0.25 mmol) in diethyl ether (3 mL) under argon was treated with phenyllithium (0.050 mL, 0.10 mmol; 2.0 M solution in dibutyl ether) and the reaction mixture stirred at 0° C. After 1 h, the reaction mixture was quenched by addition of a sat. aq. solution of ammonium chloride (10 mL) and the aq. phase extracted with EtOAc (3×10 mL). The combined organic phases were dried over MgSO₄ and concentrated under reduced pressure. Purification by preparative HPLC on reversed phase eluting with a gradient of acetonitrile-water provided the title compound as light brown oil (3.3 mg, 10%). MS: 374.2 (M+H)⁺.

Example 5

(rac)-4-[2-Fluoro-4-(trifluoromethyl)phenyl]-6,7-dihydro-5H-cyclopenta[c]pyridin-5-ol

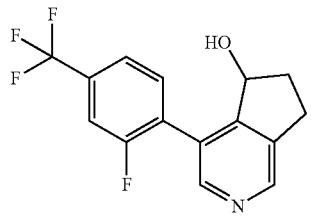

In analogy to the procedure described for the preparation of (rac)-4-(3-fluoro-4-(trifluoromethyl)phenyl)-6,7-dihydro-5H-cyclopenta[c]pyridin-5-ol (example 2), replacing 4-(3-fluoro-4-trifluoromethyl-phenyl)-6,7-dihydro-[2]pyrindin-5-one (intermediate A-1) with 4-[2-fluoro-4-(trifluoromethyl)phenyl]-6,7-dihydrocyclopenta[c]pyridin-5-one (intermediate A-2). The title compound was obtained as white solid (10.6 mg, 66%). MS: 298.1 (M+H)⁺.

Example 6

(rac)-4-[2-Fluoro-4-(trifluoromethyl)phenyl]-5-methyl-6,7-dihydrocyclopenta[c]pyridin-5-ol

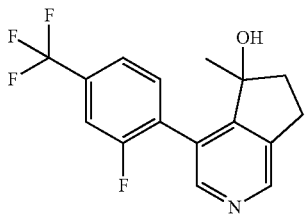 [SMILES: CC1(O)CCc2cncc(-c3ccc(C(F)(F)F)cc3F)c21]

In analogy to the procedure described for the preparation of (rac)-4-(3-fluoro-4-(trifluoromethyl)phenyl)-5-methyl-6,7-dihydro-5H-cyclopenta[c]pyridin-5-ol (example 3), replacing 4-(3-fluoro-4-trifluoromethyl-phenyl)-6,7-dihydro-[2]pyrindin-5-one (intermediate A-1) with 4-[2-fluoro-4-(trifluoromethyl)phenyl]-6,7-dihydrocyclopenta[c]pyridin-5-one (intermediate A-2). Purification by preparative TLC (EtOAc-n-heptane=1:1) provided the title compound as white solid (6.1 mg, 23%). MS: 312.1 (M+H)$^+$.

Example 7

(rac)-4-[2-Fluoro-4-(trifluoromethyl)phenyl]-5-isopropyl-6,7-dihydrocyclopenta[c]pyridin-5-ol

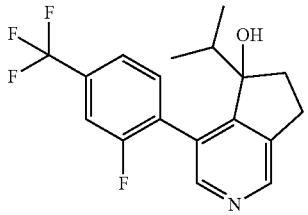 [SMILES: CC(C)C1(O)CCc2cncc(-c3ccc(C(F)(F)F)cc3F)c21]

A solution of isopropylmagnesium chloride (0.044 mL, 0.088 mmol; 2.0 M solution in THF) in THF (1 mL) under argon was treated with isopropylmagnesium chloride (0.044 mL, 0.088 mmol; 2.0 M solution in THF) at rt for 1 h. The reaction mixture was cooled to 0° C. and a solution of 4-[2-fluoro-4-(trifluoromethyl)phenyl]-6,7-dihydrocyclopenta[c]pyridin-5-one (intermediate A-2) (20 mg, 0.068 mmol) in THF (2 mL) was added. After 2 h, the reaction mixture was quenched by addition of a sat. aq. solution of ammonium chloride (10 mL) and the aq. phase extracted with EtOAc (3×10 mL). The combined organic phases were dried over MgSO$_4$ and concentrated under reduced pressure. Purification by preparative HPLC on reversed phase eluting with a gradient of acetonitrile-water provided the title compound as off-white solid (5.0 mg, 22%). MS: 340.1 (M+H)$^+$.

Example 8

(rac)-4-[2-Fluoro-4-(trifluoromethyl)phenyl]-5-phenyl-6,7-dihydrocyclopenta[c]pyridin-5-ol

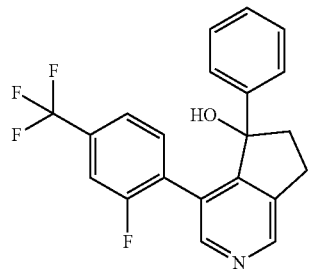 [SMILES: OC1(c2ccccc2)CCc2cncc(-c3ccc(C(F)(F)F)cc3F)c21]

In analogy to the procedure described for the preparation of (rac)-4-(3-fluoro-4-(trifluoromethyl)phenyl)-5-phenyl-6,7-dihydro-5H-cyclopenta[c]pyridin-5-ol (example 4), replacing 4-(3-fluoro-4-trifluoromethyl-phenyl)-6,7-dihydro-[2]pyrindin-5-one (intermediate A-1) with 4-[2-fluoro-4-(trifluoromethyl)phenyl]-6,7-dihydrocyclopenta[c]pyridin-5-one (intermediate A-2). Purification by preparative HPLC on reversed phase eluting with a gradient of acetonitrile-water provided the title compound as light brown solid (5.0 mg, 15%). MS: 374.1 (M+H)$^+$.

Example 9 and Example 10

(+)-4-[2-Fluoro-4-(trifluoromethyl)phenyl]-5-phenyl-6,7-dihydrocyclopenta[c]pyridin-5-ol and (−)-4-[2-Fluoro-4-(trifluoromethyl)phenyl]-5-phenyl-6,7-dihydrocyclopenta[c]pyridin-5-ol Example 9

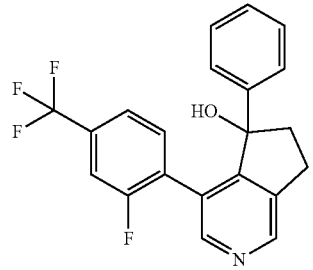

(+)

Example 10

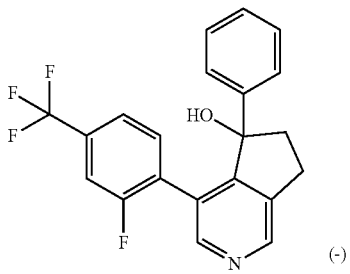

(−)

The title compounds were prepared by chiral separation of (rac)-4-[2-fluoro-4-(trifluoromethyl)phenyl]-5-phenyl-6,7-dihydrocyclopenta[c]pyridin-5-ol (227 mg, 0.61 mmol; example 8) on a Reprosil Chiral NR column (isopropanol-n-heptane=1:4) to give (+)-(R or S)-4-[2-fluoro-4-(trifluoromethyl)phenyl]-5-phenyl-6,7-dihydrocyclopenta[c]pyridin-5-ol [64.2 mg, 28%; MS: 374.1 (M+H)⁺; example 9] and (−)-(R or S)-4-[2-fluoro-4-(trifluoromethyl)phenyl]-5-phenyl-6,7-dihydrocyclopenta[c]pyridin-5-ol [63.0 mg, 27%; MS: 374.1 (M+H)⁺; example 10] as off-white foams.

Example 11

(rac)-Ethyl 2-[4-[3-fluoro-4-(trifluoromethyl)phenyl]-6,7-dihydro-5H-cyclopenta[c]pyridin-5-yl]acetate

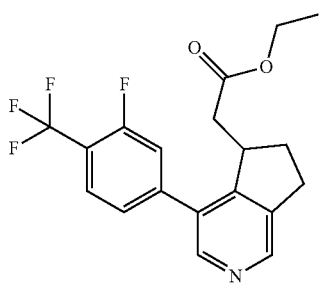 [SMILES: CCOC(=O)CC1CCc2cncc(-c3ccc(C(F)(F)F)c(F)c3)c21]

A solution of (rac)-2-[4-[3-fluoro-4-(trifluoromethyl)phenyl]-6,7-dihydro-5H-cyclopenta[c]pyridin-5-yl]acetic acid and (rac)-2-[4-[3-fluoro-4-(trifluoromethyl)phenyl]-6,7-dihydro-5H-cyclopenta[c]pyridin-7-yl]acetic acid one (intermediate A-3) (67.9 mg, 0.20 mmol) and N,N-diisopropylethylamine (0.17 mL, 1.0 mmol) in DMF (0.4 mL) and ethanol (0.4 mL) under argon was treated with HATU (98.9 mg, 0.26 mmol) at rt for 2 h. Evaporation of the solvent mixture and purification by preparative HPLC on reversed phase eluting with a gradient of acetonitrile-water provided the title compound as light brown solid (6.2 mg, 17%). MS: 368.1 (M+H)⁺.

Example 12

(rac)-2-[4-[3-Fluoro-4-(trifluoromethyl)phenyl]-6,7-dihydro-5H-cyclopenta[c]pyridin-5-yl]-N-methyl-acetamide

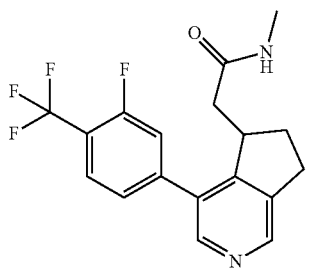 [SMILES: CNC(=O)CC1CCc2cncc(-c3ccc(C(F)(F)F)c(F)c3)c21]

A solution of (rac)-2-[4-[3-fluoro-4-(trifluoromethyl)phenyl]-6,7-dihydro-5H-cyclopenta[c]pyridin-5-yl]acetic acid and (rac)-2-[4-[3-fluoro-4-(trifluoromethyl)phenyl]-6,7-dihydro-5H-cyclopenta[c]pyridin-7-yl]acetic acid one (intermediate A-3) (50 mg, 0.15 mmol) and N,N-diisopropylethylamine (0.13 mL, 0.74 mmol) in DMF (0.4 mL) under argon was treated with HATU (72.9 mg, 0.19 mmol). To this solution was added methylamine (0.22 mL, 0.44 mmol; 2.0 M solution in THF) and the reaction mixture stirred at rt for 16 h. Evaporation of the solvent mixture and purification by preparative HPLC on reversed phase eluting with a gradient of acetonitrile-water provided the title compound as light brown solid (8.0 mg, 30%). MS: 353.1 (M+H)⁺.

Example 13

(rac)-N-(Cyclopropylmethyl)-2-[4-[3-fluoro-4-(trifluoromethyl)phenyl]-6,7-dihydro-5H-cyclopenta[c]pyridin-5-yl]acetamide

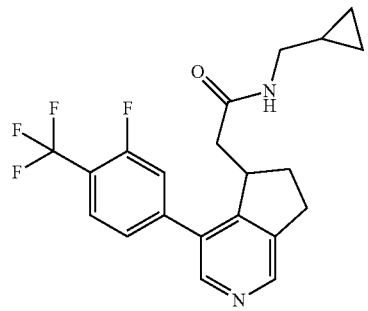 [SMILES: O=C(CC1CCc2cncc(-c3ccc(C(F)(F)F)c(F)c3)c21)NCC1CC1]

In analogy to the procedure described for the preparation of (rac)-2-[4-[3-fluoro-4-(trifluoromethyl)phenyl]-6,7-dihydro-5H-cyclopenta[c]pyridin-5-yl]-N-methyl-acetamide (example 12), replacing methylamine with cyclopropylmethylamine. Evaporation of the solvent mixture and purification by preparative HPLC on reversed phase eluting with a gradient of acetonitrile-water provided the title compound as light yellow solid (6.0 mg, 20%). MS: 393.2 (M+H)⁺.

Example 14

(rac)-2-[4-[3-Fluoro-4-(trifluoromethyl)phenyl]-6,7-dihydro-5H-cyclopenta[c]pyridin-5-yl]-N-propyl-acetamide

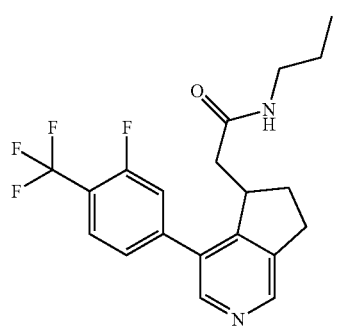 [SMILES: CCCNC(=O)CC1CCc2cncc(-c3ccc(C(F)(F)F)c(F)c3)c21]

In analogy to the procedure described for the preparation of (rac)-2-[4-[3-fluoro-4-(trifluoromethyl)phenyl]-6,7-dihydro-5H-cyclopenta[c]pyridin-5-yl]-N-methyl-acetamide (example 12), replacing methylamine with propylamine.

Evaporation of the solvent mixture and purification by preparative HPLC on reversed phase eluting with a gradient of acetonitrile-water provided the title compound as light brown solid (2.0 mg, 4%). MS: 381.6 (M+H)+.

Example 14

(rac)-2-[4-[3-Fluoro-4-(trifluoromethyl)phenyl]-6,7-dihydro-5H-cyclopenta[c]pyridin-5-yl]-1-(1-piperidyl)ethanone

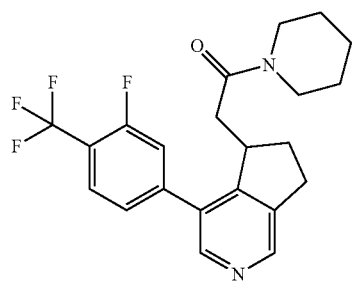 [SMILES: O=C(CC1CCc2cncc(-c3ccc(C(F)(F)F)c(F)c3)c21)N1CCCCC1]

In analogy to the procedure described for the preparation of (rac)-2-[4-[3-fluoro-4-(trifluoromethyl)phenyl]-6,7-dihydro-5H-cyclopenta[c]pyridin-5-yl]-N-methyl-acetamide (example 12), replacing methylamine with piperidine. Evaporation of the solvent mixture and purification by preparative HPLC on reversed phase eluting with a gradient of acetonitrile-water provided the title compound as light brown solid (4.8 mg, 16%). MS: 407.6 (M+H)+.

Example 16

(rac)-2-[4-[3-Fluoro-4-(trifluoromethyl)phenyl]-6,7-dihydro-5H-cyclopenta[c]pyridin-5-yl]-1-morpholino-ethanone

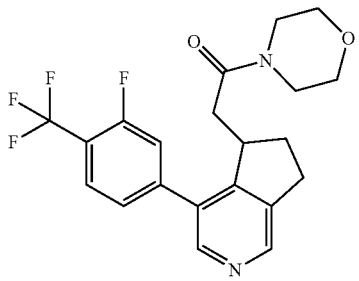 [SMILES: O=C(CC1CCc2cncc(-c3ccc(C(F)(F)F)c(F)c3)c21)N1CCOCC1]

In analogy to the procedure described for the preparation of (rac)-2-[4-[3-fluoro-4-(trifluoromethyl)phenyl]-6,7-dihydro-5H-cyclopenta[c]pyridin-5-yl]-N-methyl-acetamide (example 12), replacing methylamine with morpholine. Evaporation of the solvent mixture and purification by preparative HPLC on reversed phase eluting with a gradient of acetonitrile-water provided the title compound as light brown solid (4.2 mg, 14%). MS: 409.6 (M+H)+.

Example 17

(rac)-2-[4-[3-Fluoro-4-(trifluoromethyl)phenyl]-6,7-dihydro-5H-cyclopenta[c]pyridin-5-yl]-N-isoxazol-3-yl-acetamide

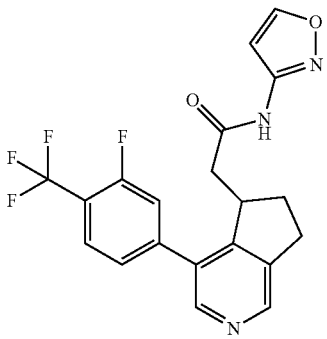 [SMILES: O=C(CC1CCc2cncc(-c3ccc(C(F)(F)F)c(F)c3)c21)Nc1ccon1]

In analogy to the procedure described for the preparation of (rac)-2-[4-[3-fluoro-4-(trifluoromethyl)phenyl]-6,7-dihydro-5H-cyclopenta[c]pyridin-5-yl]-N-methyl-acetamide (example 12), replacing methylamine with isoxazol-3-amine. Evaporation of the solvent mixture and purification by preparative HPLC on reversed phase eluting with a gradient of acetonitrile-water provided the title compound as light brown solid (6.6 mg, 22%). MS: 406.1 (M+H)+.

Example 18

(rac)-2-[4-[3-Fluoro-4-(trifluoromethyl)phenyl]-6,7-dihydro-5H-cyclopenta[c]pyridin-5-yl-]-N-(1H-pyrazol-3-yl)acetamide

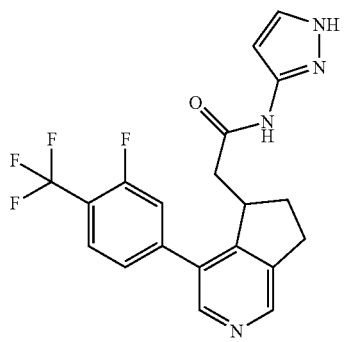 [SMILES: O=C(CC1CCc2cncc(-c3ccc(C(F)(F)F)c(F)c3)c21)Nc1cc[nH]n1]

In analogy to the procedure described for the preparation of (rac)-2-[4-[3-fluoro-4-(trifluoromethyl)phenyl]-6,7-dihydro-5H-cyclopenta[c]pyridin-5-yl]-N-methyl-acetamide (example 12), replacing methylamine with 1H-pyrazol-3-amine. Evaporation of the solvent mixture and purification by preparative HPLC on reversed phase eluting with a gradient of acetonitrile-water provided the title compound as light brown solid (10.4 mg, 34%). MS: 405.1 (M+H)+.

Example 19

(rac)-2-[4-[2-Fluoro-4-(trifluoromethyl)phenyl]-6,7-dihydro-5H-cyclopenta[c]pyridin-5-yl]-1-pyrrolidin-1-yl-ethanone

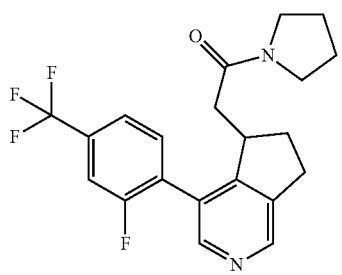 [SMILES: O=C(CC1CCc2cncc(-c3ccc(C(F)(F)F)cc3F)c21)N1CCCC1]

In analogy to the procedure described for the preparation of (rac)-2-[4-[3-fluoro-4-(trifluoromethyl)phenyl]-6,7-dihydro-5H-cyclopenta[c]pyridin-5-yl]-N-methyl-acetamide (example 12), replacing (rac)-2-[4-[3-fluoro-4-(trifluoromethyl)phenyl]-6,7-dihydro-5H-cyclopenta[c]pyridin-5-yl]acetic acid and (rac)-2-[4-[3-fluoro-4-(trifluoromethyl)phenyl]-6,7-dihydro-5H-cyclopenta[c]pyridin-7-yl]acetic acid one (intermediate A-3) with (rac)-2-[4-[2-fluoro-4-(trifluoromethyl)phenyl]-6,7-dihydro-5H-cyclopenta[c]pyridin-5-yl]acetic acid and (rac)-2-[4-[2-fluoro-4-(trifluoromethyl)phenyl]-6,7-dihydro-5H-cyclopenta[c]pyridin-7-yl]acetic acid one (intermediate A-4) and methylamine with pyrrolidine. Evaporation of the solvent mixture and purification by preparative HPLC on reversed phase eluting with a gradient of acetonitrile-water and preparative TLC on normal phase (DCM-MeOH=93:7) provided the title compound as white solid (2.2 mg, 8%). MS: 393.2 (M+H)⁺.

Example 20

(rac)-N-Ethyl-2-[4-[2-fluoro-4-(trifluoromethyl)phenyl]-6,7-dihydro-5H-cyclopenta[c]pyridin-5-yl-]-N-methyl-acetamide

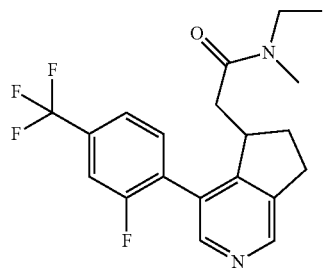 [SMILES: CCN(C)C(=O)CC1CCc2cncc(-c3ccc(C(F)(F)F)cc3F)c21]

In analogy to the procedure described for the preparation of (rac)-2-[4-[2-fluoro-4-(trifluoromethyl)phenyl]-6,7-dihydro-5H-cyclopenta[c]pyridin-5-yl]-1-pyrrolidin-1-yl-ethanone (example 19), replacing pyrrolidine with N-methylethanamine. Evaporation of the solvent mixture and purification by preparative HPLC on reversed phase eluting with a gradient of acetonitrile-water and preparative TLC on normal phase (DCM-MeOH=93:7) provided the title compound as white solid (2.4 mg, 9%). MS: 381.2 (M+H)⁺.

Example 21

(rac)-2-[4-[2-Fluoro-4-(trifluoromethyl)phenyl]-6,7-dihydro-5H-cyclopenta[c]pyridin-5-yl]-N-isopropyl-N-methyl-acetamide

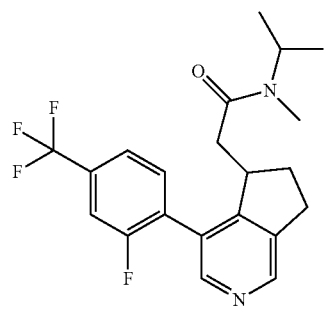 [SMILES: CC(C)N(C)C(=O)CC1CCc2cncc(-c3ccc(C(F)(F)F)cc3F)c21]

In analogy to the procedure described for the preparation of (rac)-2-[4-[2-fluoro-4-(trifluoromethyl)phenyl]-6,7-dihydro-5H-cyclopenta[c]pyridin-5-yl]-1-pyrrolidin-1-yl-ethanone (example 19), replacing pyrrolidine with N-methylpropan-2-amine. Evaporation of the solvent mixture and purification by preparative HPLC on reversed phase eluting with a gradient of acetonitrile-water and preparative TLC on normal phase (DCM-MeOH=93:7) provided the title compound as white solid (2.2 mg, 8%). MS: 395.2 (M+H)⁺.

Example 22

(rac)-N-Cyclopropyl-2-[4-[2-fluoro-4-(trifluoromethyl)phenyl]-6,7-dihydro-5H-cyclopenta[c]pyridin-5-yl-]-N-methyl-acetamide

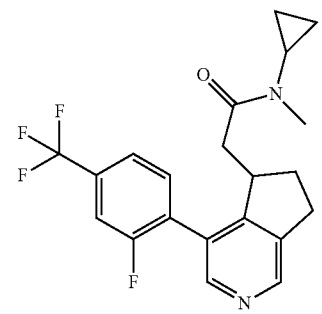 [SMILES: CN(C(=O)CC1CCc2cncc(-c3ccc(C(F)(F)F)cc3F)c21)C1CC1]

In analogy to the procedure described for the preparation of (rac)-2-[4-[2-fluoro-4-(trifluoromethyl)phenyl]-6,7-dihydro-5H-cyclopenta[c]pyridin-5-yl]-1-pyrrolidin-1-yl-ethanone (example 19), replacing pyrrolidine with N-methylcyclopropanamine. Evaporation of the solvent mixture and purification by preparative HPLC on reversed phase eluting with a gradient of acetonitrile-water and preparative TLC on normal phase (DCM-MeOH=93:7) provided the title compound as white solid (1.4 mg, 5%). MS: 393.2 (M+H)⁺.

Example 23

(rac)-N-Cyclopropyl-N-ethyl-2-[4-[2-fluoro-4-(trifluoromethyl)phenyl]-6,7-dihydro-5H-cyclopenta[c]pyridin-5-yl]acetamide

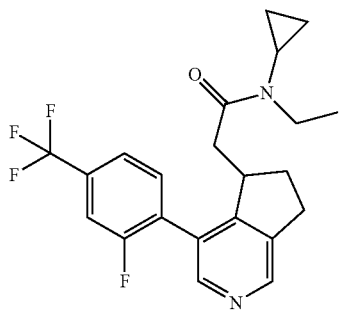 [SMILES: CCN(C(=O)CC1CCc2cncc(-c3ccc(C(F)(F)F)cc3F)c21)C1CC1]

In analogy to the procedure described for the preparation of (rac)-2-[4-[2-fluoro-4-(trifluoromethyl)phenyl]-6,7-dihydro-5H-cyclopenta[c]pyridin-5-yl]-1-pyrrolidin-1-yl-ethanone (example 19), replacing pyrrolidine with N-ethylcyclopropanamine. Evaporation of the solvent mixture and purification by preparative HPLC on reversed phase eluting with a gradient of acetonitrile-water and preparative TLC on normal phase (DCM-MeOH=93:7) provided the title compound as white solid (2.4 mg, 8%). MS: 407.2 (M+H)$^+$.

Example 24

(rac)-2-[4-[2-Fluoro-4-(trifluoromethyl)phenyl]-6,7-dihydro-5H-cyclopenta[c]pyridin-5-yl]-1-[(2S)-2-methylpyrrolidin-1-yl]ethanone

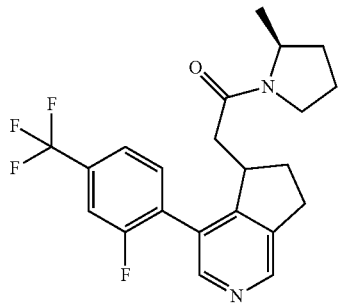 [SMILES: C[C@H]1CCCN1C(=O)CC1CCc2cncc(-c3ccc(C(F)(F)F)cc3F)c21]

In analogy to the procedure described for the preparation of (rac)-2-[4-[2-fluoro-4-(trifluoromethyl)phenyl]-6,7-dihydro-5H-cyclopenta[c]pyridin-5-yl]-1-pyrrolidin-1-yl-ethanone (example 19), replacing pyrrolidine with (2S)-2-methylpyrrolidine. Evaporation of the solvent mixture and purification by preparative HPLC on reversed phase eluting with a gradient of acetonitrile-water and preparative TLC on normal phase (DCM-MeOH=93:7) provided the title compound as white solid (2.3 mg, 7%). MS: 407.2 (M+H)$^+$.

Example A

A compound of formula (I) can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:
1. A compound of formula (I)

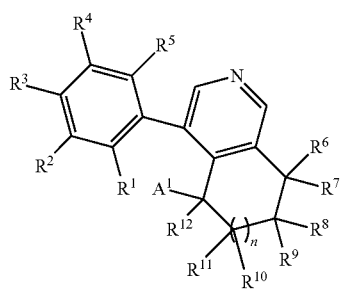

wherein $R^1$, $R^2$ $R^4$ and $R^5$ are independently selected from H, halogen, cyano, nitro, alkyl, haloalkyl, cycloalkyl, alkoxy, haloalkoxy and cycloalkoxy;

$R^3$ is haloalkyl;

$R^6$, $R^7$, $R^8$, $R^9$, $R^{10}$ and $R^{11}$ are independently selected from H, halogen, alkyl and haloalkyl;

$R^{12}$ is H, alkyl, haloalkyl, cycloalkyl, substituted aryl or substituted heteroaryl, wherein substituted aryl or substituted heteroaryl are substituted with $R^{18}$, $R^{19}$ and $R^{20}$;

$A^1$ is —(CR$^{14}$R$^{15}$)$_p$—NR$^{16}$R$^{17}$, —(CR$^{14}$R$^{15}$)$_p$—OR$^{17}$, —(CR$^{14}$R$^{15}$)$_p$—C(O)NR$^{16}$R$^{17}$ or —(CR$^{14}$R$^{15}$)$_p$—C(O)OR$^{17}$;

$R^{14}$ and $R^{15}$ are independently selected from H, alkyl, haloalkyl, cycloalkyl and halocycloalkyl;

$R^{16}$ is H, alkyl, haloalkyl, cycloalkyl, hydroxyalkyl, alkoxyalkyl or haloalkoxyalkyl;

$R^{17}$ is H, alkyl, haloalkyl, cycloalkyl, cycloalkylalkyl, alkoxyalkyl, cycloalkoxyalkyl, substituted aryl or substituted heteroaryl, wherein substituted aryl or substituted heteroaryl are substituted with $R^{21}$, $R^{22}$ and $R^{23}$;

or $R^{16}$ and $R^{17}$ together with the nitrogen to which they are attached form a substituted heterocycloalkyl or a substituted heteroaryl, wherein substituted heterocycloalkyl and substituted heteroaryl are substituted with $R^{21}$, $R^{22}$ and $R^{23}$;

$R^{18}$, $R^{19}$, $R^{20}$, $R^{21}$, $R^{22}$ and $R^{23}$ are independently selected from H, halogen, alkyl, haloalkyl, cycloalkyl, alkoxy and haloalkoxy;

n is zero, 1 or 2;

p is zero, 1 or 2;

and pharmaceutically acceptable salts thereof.

2. The compound of claim 1, wherein $R^1$, $R^2$, $R^4$ and $R^5$ are independently selected from H, halogen and haloalkyl.

3. The compound of claim 1, wherein $R^1$ and $R^2$ are independently selected from H and halogen.

4. The compound of claim 1, wherein $R^4$ and $R^5$ are H.

5. The compound of claim 1, wherein n is zero and $R^6$, $R^7$, $R^8$ and $R^9$ are H.

6. The compound of claim 1, wherein $R^{12}$ is H, alkyl or substituted aryl, wherein substituted aryl is substituted with $R^{18}$, $R^{19}$ and $R^{20}$.

7. The compound of claim 1, wherein $R^{18}$, $R^{19}$ and $R^{20}$ are H.

8. The compound of claim 1, wherein $A^1$ is —$(CR^{14}R^{15})_p$—$OR^{17}$ or —$(CR^{14}R^{15})_p$—$C(O)NR^{16}R^{17}$.

9. The compound of claim 1, wherein $A^1$ is —$(CR^{14}R^{15})_p$—$OR^{17}$.

10. The compound of claim 1, wherein $R^{16}$ is H.

11. The compound of claim 1, wherein $R^{17}$ is H, alkyl, alkoxyalkyl or substituted heteroaryl, wherein substituted heteroaryl is substituted with $R^{21}$, $R^{22}$ and $R^{23}$ or $R^{16}$ and $R^{17}$ together with the nitrogen to which they are attached form a substituted heterocycloalkyl, wherein substituted heterocycloalkyl is substituted with $R^{21}$, $R^{22}$ and $R^{23}$.

12. The compound of claim 1, wherein $R^{17}$ is H, alkyl, alkoxyalkyl or substituted heteroaryl, wherein substituted heteroaryl is substituted with $R^{21}$, $R^{22}$ and $R^{23}$.

13. The compound of claim 1, wherein $R^{21}$, $R^{22}$ and $R^{23}$ are independently selected from H and alkyl.

14. The compound of claim 1, wherein $R^{14}$ and $R^{15}$ are H.

15. The compound of claim 1, wherein p is zero or 1.

16. A compound selected from
4-(3-fluoro-4-(trifluoromethyl)phenyl)-6,7-dihydro-5H-cyclopenta[c]pyridin-5-amine;
4-(3-fluoro-4-(trifluoromethyl)phenyl)-6,7-dihydro-5H-cyclopenta[c]pyridin-5-ol;
4-(3-fluoro-4-(trifluoromethyl)phenyl)-5-methyl-6,7-dihydro-5H-cyclopenta[c]pyridin-5-ol;
4-(3-fluoro-4-(trifluoromethyl)phenyl)-5-phenyl-6,7-dihydro-5H-cyclopenta[c]pyridin-5-ol;
4-(2-fluoro-4-(trifluoromethyl)phenyl)-6,7-dihydro-5H-cyclopenta[c]pyridin-5-ol;
4-(2-fluoro-4-(trifluoromethyl)phenyl)-5-methyl-6,7-dihydro-5H-cyclopenta[c]pyridin-5-ol;
4-(2-fluoro-4-(trifluoromethyl)phenyl)-5-isopropyl-6,7-dihydro-5H-cyclopenta[c]pyridin-5-ol;
4-(2-fluoro-4-(trifluoromethyl)phenyl)-5-phenyl-6,7-dihydro-5H-cyclopenta[c]pyridin-5-ol;
(+)-4-(2-fluoro-4-(trifluoromethyl)phenyl)-5-phenyl-6,7-dihydro-5H-cyclopenta[c]pyridin-5-ol;
(+4-(2-fluoro-4-(trifluoromethyl)phenyl)-5-phenyl-6,7-dihydro-5H-cyclopenta[c]pyridin-5-ol;
(R)-4-(2-fluoro-4-(trifluoromethyl)phenyl)-5-phenyl-6,7-dihydro-5H-cyclopenta[c]pyridin-5-ol;
(S)-4-(2-fluoro-4-(trifluoromethyl)phenyl)-5-phenyl-6,7-dihydro-5H-cyclopenta[c]pyridin-5-ol;
ethyl 2-(4-(3-fluoro-4-(trifluoromethyl)phenyl)-6,7-dihydro-5H-cyclopenta[c]pyridin-5-yl)acetate;
2-(4-(3-fluoro-4-(trifluoromethyl)phenyl)-6,7-dihydro-5H-cyclopenta[c]pyridin-5-yl)-N-methylacetamide;
N-(cyclopropylmethyl)-2-(4-(3-fluoro-4-(trifluoromethyl)phenyl)-6,7-dihydro-5H-cyclopenta[c]pyridin-5-yl)acetamide;
2-(4-(3-fluoro-4-(trifluoromethyl)phenyl)-6,7-dihydro-5H-cyclopenta[c]pyridin-5-yl)-N-propylacetamide;
2-(4-(3-fluoro-4-(trifluoromethyl)phenyl)-6,7-dihydro-5H-cyclopenta[c]pyridin-5-yl)-1-(piperidin-1-yl)ethanone;
2-(4-(3-fluoro-4-(trifluoromethyl)phenyl)-6,7-dihydro-5H-cyclopenta[c]pyridin-5-yl)-1-morpholinoethanone;
2-[4-(3-Fluoro-4-trifluoromethyl-phenyl)-6,7-dihydro-5H-[2]pyrindin-5-yl]-N-isoxazol-3-yl-acetamide;
2-(4-(3-fluoro-4-(trifluoromethyl)phenyl)-6,7-dihydro-5H-cyclopenta[c]pyridin-5-yl)-N-(1H-pyrazol-3-yl)acetamide;
2-(4-(2-fluoro-4-(trifluoromethyl)phenyl)-6,7-dihydro-5H-cyclopenta[c]pyridin-5-yl)-1-(pyrrolidin-1-yl)ethanone;
N-ethyl-2-(4-(2-fluoro-4-(trifluoromethyl)phenyl)-6,7-dihydro-5H-cyclopenta[c]pyridin-5-yl)-N-methylacetamide;
2-(4-(2-fluoro-4-(trifluoromethyl)phenyl)-6,7-dihydro-5H-cyclopenta[c]pyridin-5-yl)-N-isopropyl-N-methylacetamide;
N-cyclopropyl-2-(4-(2-fluoro-4-(trifluoromethyl)phenyl)-6,7-dihydro-5H-cyclopenta[c]pyridin-5-yl)-N-methylacetamide;
N-cyclopropyl-N-ethyl-2-(4-(2-fluoro-4-(trifluoromethyl)phenyl)-6,7-dihydro-5H-cyclopenta[c]pyridin-5-yl)acetamide;
2-(4-(2-fluoro-4-(trifluoromethyl)phenyl)-6,7-dihydro-5H-cyclopenta[c]pyridin-5-yl)-1-((S)-2-methylpyrrolidin-1-yl)ethanone;

and pharmaceutically acceptable salts thereof.

17. A process to prepare a compound of claim 1 comprising the reaction of a compound of formula (II) in the presence of a compound of formula (III);

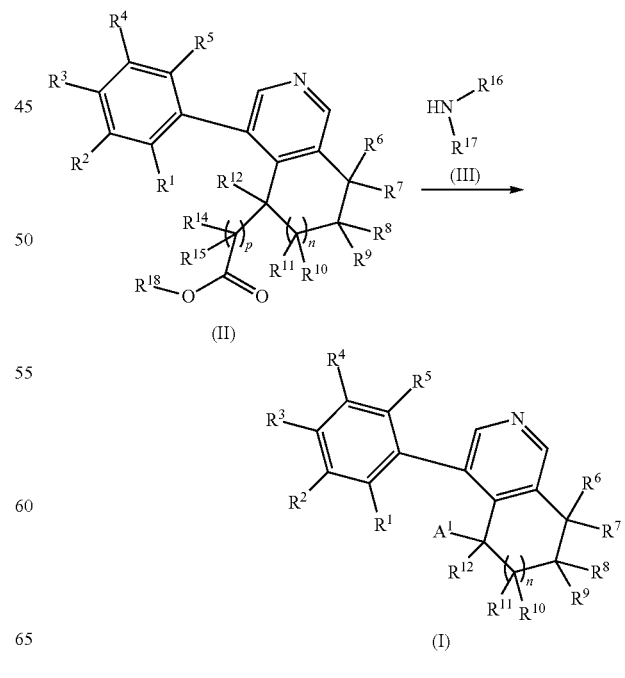

wherein $R^1$, $R^2$, $R^3$, $R^4$, $R^5$, $R^6$, $R^7$, $R^8$, $R^9$, $R^{10}$, $R^{11}$, $R^{12}$, $R^{14}$, $R^{15}$, $R^{16}$, $R^{17}$, n and p are as defined herein, $R^{24}$ is alkyl and $A^1$ is —$(CR^{14}R^{15})$—$C(O)NR^{16}R^{17}$.

18. A pharmaceutical composition comprising a compound of claim 1 and a therapeutically inert carrier.

19. A method for the treatment or prophylaxis chronic kidney disease, congestive heart failure, hypertension, primary aldosteronism and Cushing syndrom, which method comprises administering an effective amount of a compound of claim 1 to a subject in need thereof.

* * * * *